United States Patent [19]

Dower et al.

[11] Patent Number: 6,165,717

[45] Date of Patent: *Dec. 26, 2000

[54] METHOD OF SYNTHESIZING DIVERSE COLLECTIONS OF OLIGOMERS

[75] Inventors: William J. Dower, Menlo Park; Ronald W. Barrett, Sunnyvale; Mark A. Gallop, E. Palo Alto, all of Calif.

[73] Assignee: Affymax Technologies N.V., Greenford, United Kingdom

[*] Notice: This patent is subject to a terminal disclaimer.

[21] Appl. No.: 09/078,403

[22] Filed: May 13, 1998

Related U.S. Application Data

[60] Continuation of application No. 08/484,505, Jun. 7, 1995, Pat. No. 5,789,162, which is a division of application No. 07/762,522, Sep. 18, 1991, abandoned.

[51] Int. Cl.[7] ............................. C12Q 1/68; G01N 33/00; A61K 38/00; C07K 5/00; C07H 21/04
[52] U.S. Cl. ............................. 435/6; 436/94; 530/334; 536/25.3
[58] Field of Search ........................... 435/6; 436/94; 530/334; 536/25.3

[56] References Cited

U.S. PATENT DOCUMENTS

| | | | |
|---|---|---|---|
| 4,182,654 | 1/1980 | Royer | 435/272 |
| 4,315,074 | 2/1982 | Royer | 435/70 |
| 4,587,044 | 5/1986 | Miller et al. | 530/211 |
| 4,631,211 | 12/1986 | Houghten | 428/35 |
| 4,671,941 | 6/1987 | Niina et al. | 422/131 |
| 4,701,304 | 10/1987 | Horn et al. | 422/62 |
| 4,713,326 | 12/1987 | Dattagupta et al. | 435/6 |
| 4,755,558 | 7/1988 | Kalbag | 525/54.1 |
| 4,794,150 | 12/1988 | Steel | 525/54.11 |
| 4,818,681 | 4/1989 | Dattagupta | 435/6 |
| 4,833,092 | 5/1989 | Geysen | 436/501 |
| 4,855,225 | 8/1989 | Fung et al. | 435/6 |
| 4,965,188 | 10/1990 | Mullis et al. | 435/6 |
| 5,143,854 | 9/1992 | Pirrung et al. | 436/518 |
| 5,264,563 | 11/1993 | Huse | 536/25.3 |
| 5,510,240 | 4/1996 | Lam et al. | 435/7.1 |
| 5,639,603 | 6/1997 | Dower et al. | 435/6 |
| 5,708,153 | 1/1998 | Dower et al. | 536/22.1 |
| 5,770,358 | 6/1998 | Dower et al. | 435/6 |
| 5,770,455 | 6/1998 | Cargill et al. | 436/518 |
| 5,789,162 | 8/1998 | Dower et al. | 435/6 |

FOREIGN PATENT DOCUMENTS

| | | | |
|---|---|---|---|
| 0 392 546 A2 | 12/1990 | European Pat. Off. | C12Q 1/68 |
| WO 90/00626 | 1/1990 | WIPO | C12Q 1/68 |
| WO 90/14441 | 11/1990 | WIPO | C12Q 1/68 |
| WO 90/15070 | 12/1990 | WIPO | C07K 1/04 |
| WO 92/00091 | 1/1992 | WIPO | A61K 37/02 |
| WO 92/03461 | 3/1992 | WIPO | C07H 17/00 |
| WO 92/06176 | 4/1992 | WIPO | C12N 1/24 |
| WO 92/10092 | 6/1992 | WIPO | A01N 1/02 |
| WO 93/20242 | 10/1993 | WIPO | C12Q 1/70 |
| WO 94/02515 | 2/1994 | WIPO | C07K 17/06 |
| WO 94/08051 | 4/1994 | WIPO | C12Q 1/68 |

OTHER PUBLICATIONS

*Advances in Analytical Chemistry and Instrumentation*, Charles N. Reilley, Ed., John Wiley & Sons, Inc., 1964, pp. 56–59.

Amato, 1992, *Science*, 257:330–331 Speeding up a chemical game of chance.

Arnold et al., Mar. 15, 1991, *Optics Letters* 16(6):420–422 Room–temperature microparticle–based persistent spectral hole burning memory.

Baldwin et al., 1990, *Tetrahedron* 46(19):6879–6884 New photolabile phosphate protecting groups.

(List continued on next page.)

*Primary Examiner*—Kenneth R. Horlick
*Attorney, Agent, or Firm*—Lauren L. Stevens; William M. Smith

[57] ABSTRACT

A general stochastic method for synthesizing random oligomers on particles is disclosed. A further aspect of the invention relates to the use of identification tags on the particles to facilitate identification of the sequence of the monomers in the oligomer.

17 Claims, 6 Drawing Sheets

OTHER PUBLICATIONS

Barr et al., 1986, *BioTechniques* 4(5):428–432, 7–Deaza–2'–deoxyguanosine–5'–triphosphate: Enhanced resolution in M13 dideoxy sequencing.

Bashkin et al., 1991, *J. Org. Chem.* 56:3168–3176 Synthesis and characterization of oligonucleotide peptides.

Borchardt et al., 1994, *J. Am. Chem. Soc.* 116:373–374 Synthetic receptor binding elucidated with an encoded combinatorial library.

Brenner et al., 1992, *Proc. Natl. Acad. Sci. USA* 89:5381–5383 Encoded combinatorial chemistry.

Cwirla et al., 1990, *Proc. Natl. Acad. Sci. USA* 87:6378–6382 Peptides on phage: A vast library of peptides for indentifying ligands.

Eritja et al., 1991, *Tetrahedron* 47(24):4113–4120, Synthesis of defined peptide–oligonucleotide hybrids containing a nuclear transport signal sequence.

Fodor et al., 1991, *Science* 251:767–773 Light–directed, spatially addressable parallel chemical synthesis.

Frank and Doring, 1988, *Tetrahedron* 44(19):6031–6040 Simultaneous multiple peptide synthesis under continuous flow conditions on cellulose paper discs as segmental solid supports.

Frank et al., 1983, *Nuc. Acids. Res.* 11(13):4365–4377 A new general approach for the simultaneous chemical synthesis of large numbers of oligonucleotides: Segmental solid supports.

Frank et al., 1990, *Peptides* (Giralt & Andreu, eds., ESCOM Science Pub.), pp. 151–152 Facile and rapid 'spot–synthesis' of large numbers of peptides on membrane sheets.

Furka et al., Jul. 10–15, 1988, *14th Intl. Congress of Biochemistry,* Prague, Czechoslovakia, Abstract No. FR:013 Proteins and nucleic acids in three dimensions: Cornucopia of peptides by synthesis.

Furka et al., Aug. 15–19, 1988, *Xth Intl. Symp. on Medicinal Chem.,* Budapest, Hungary, Abstract No. P–168, p. 288 More peptides by less labour.

Furka et al., 1991, *Int. J. Peptide Protein Res.,* 37:487–493 General method for rapid synthesis of multicomponent peptide mixtures.

Geysen et al., 1987, *J. Immunol. Meth.,* 102:259–274 Strategies for epitope analysis using peptide synthesis.

Geysen et al., 1984, *Proc. Natl. Acad. Sci. USA,* 81:3998–4002 Use of peptide synthesis to probe viral antigens for epitopes to a resolution of a single amino acid.

Haralambidis et al., 1990, *Nuc. Acids Res.* 18(3):493–505 The synthesis of polyamide–oligonucleotide conjugate molecules.

Hayakawa et al., 1990, *J. Am. Chem. Soc.* 112:1691–1696 The allylic protection method in solid–phase oligonecleotide synthesis: An efficient preparation of solid–anchored DNA Oligomers.

Hodgson, 1992, *Bio/Technology* 10:973–974 Receptor screening and the search for new pharmaceuticals.

Houghten et al., 1991, *Nature* 354:84–86 Generation and use of synthetic peptide combinatorial libraries for basic research and drug discovery.

Houghten, 1985, *Proc. Natl. Acad. Sci. USA* 82:5131–5135 General method for the rapid solid–phase synthesis of large numbers of peptides: Specificity of antigen–antibody interaction at the level of individual amino acids.

Juby et al., 1991, *Tetrahedron Letters* 32(7):879–882 Facile preparation of 3' oligonucleotide–peptide conjugates.

Kaiser et al., 1989, *Science* 243:187–192 Peptide and protein synthesis by segment synthesis–condensation.

Kerr et al., 1993, *J. Am Chem Soc.,* 115:2529–2531 Encoded combinatorial peptide libraries containing non–natural amino acids.

Lam et al., 1991, *12th Amer. Pep. Symp.,* Abstract LW3 Rapid selection and structure determination of acceptor binding ligands from a large synthetic peptide library.

Lam et al., 1991, *Nature* 354:82–84 A new type of synthetic peptide library for indentifying ligand–binding activity.

Mathur et al., 1980, *Polymers as Aids in Organic Chemistry,* Academic Press, New York, Ch. 9–12:138–197.

Needels et al., 1993, *Proc. Natl. Acad. Sci. USA,* 90:10700–10704 Generation and screening of an oligonucleotide–encoded sythetic peptide library.

Nikolaiev et al., 1993, Peptide Research, 6(3):161–170 Peptide–encoding for structure determination of nonsequenceable polymers within libraries synthesized and tested on solid phase supports.

Ohlmeyer et al., 1993, *Proc. Natl. Acad. Sci. USA,* 90:10922–10926 Complex synthetic chemical libraries indexed with molecular tags.

Tjoeng et al., 1990, *Int. J. Pept. Protein Res.* 35:141–146 Multiple peptide synthesis using a single support (MPS3).

Van der Zee et al., 1989, *Eur. J. Immunol.* 19:43–48 Efficient mapping and characterization of a T cell epitope by the simultaneous synthesis of multiple peptides.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Gly Gly Phe Leu
1

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS: single

```
        (D) TOPOLOGY: linear (ii) MOLECULE TYPE: peptide (xi) SEQUENCE DESCRIPTION: SEQ ID NO:2:

Pro Gly Phe Leu
1

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2...0
        (D) OTHER INFORMATION: Xaa is Gly or Pro (xi) SEQUENCE DESCRIPTION: SEQ ID NO:3:

Tyr Xaa Gly Pro Leu
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2...0
        (D) OTHER INFORMATION: Xaa is Gly or Pro (xi) SEQUENCE DESCRIPTION: SEQ ID NO:4:

Pro Xaa Gly Phe Leu
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Tyr Gly Gly Phe Leu
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:
```

```
Tyr Pro Gly Phe Leu
1               5
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Pro Pro Gly Phe Leu
1               5
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Pro Gly Gly Phe Leu
1               5
```

(2) INFORMATION FOR SEQ ID NO:9:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CTTTCTTCCT CTCCCTCTTT TCTCCTCTCT TTTTTTCTCC TTCTTTTTTT CTCTCCCTCT    60
CTCCTCTCTC CCCCTTTCTC TCCTTTCCTC CTCTCCTCTC TCTCTTCTTC C            111
```

(2) INFORMATION FOR SEQ ID NO:10:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CTTTCTTCCT CTCCCTCTTT TCTCCTCTTC TTTTTTCTCC TTTCTTTTTT CTCTCCCTCT    60
CTCCTCTCTC CCCTTTCTCT CCTTTCCTCC TCTCCTCTCT CTCTTCTTTC C            111
```

(2) INFORMATION FOR SEQ ID NO:11:

(i) SEQUENCE CHARACTERISTICS:
        (A) LENGTH: 115 base pairs
        (B) TYPE: nucleic acid
        (C) STRANDEDNESS: single
        (D) TOPOLOGY: linear

```
    (ii) MOLECULE TYPE: cDNA (xi) SEQUENCE DESCRIPTION: SEQ ID NO:11:

CTTTCTTCCT CTCCCTCTTT TCTCCTCTTT CTTTTTCTCC TTTTCTTTTT CTCTCCCTCT        60

CTCCTCTCTC TCTTCCTTTC CCCTCTCTCT CTCCTCTCCT CTCTCTCTTC TTTCC           115

(2) INFORMATION FOR SEQ ID NO:12:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CTTTCTTCCT CTCCCTCTTT TCTCCTCTTC TTTTTTCTCC TTTCTTTTTT CTCTCCCTCT        60

CTCCTCTCTC TCTTCCTTTC CCCTCTCTCT CTCCTCTCCT CTCTCTCTTC TTTCC           115

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TCCTCTCCCT CTTTTCTCCT CCT                                               23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGAAAGAAGA GGGAAAGGAG AGG                                               23

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

AGAGAGGGGA AAGGAAGA                                                     18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

-continued

```
   (ii) MOLECULE TYPE: cDNA (xi) SEQUENCE DESCRIPTION: SEQ ID NO:16:

AGGAAAGGAG AGAAAGGG                                                       18
```

METHOD OF SYNTHESIZING DIVERSE COLLECTIONS OF OLIGOMERS

This application is a continuation of application Ser. No. 08/484,505 filed Jun. 7, 1995, now U.S. Pat. No. 5,789,162, which is a division of application Ser. No. 07/762,522 filed Sep. 18, 1991, now abandoned.

FIELD OF THE INVENTION

The present invention relates generally to a general stochastic method for synthesizing random oligomers on particles. A further aspect of the invention relates to the use of identification tags on the particles to facilitate identification of the oligomer sequence.

BACKGROUND OF THE INVENTION

The relationship between structure and activity of molecules is a fundamental issue in the study of biological systems. Structure-activity relationships are important in understanding, for example, the function of enzymes, the ways in which cells communicate with each other, as well as cellular control and feedback systems. Certain macromolecules are known to interact and bind to other molecules having a very specific three-dimensional spatial and electronic distribution. Any large molecule having such specificity can be considered a receptor, whether it is an enzyme catalyzing hydrolysis of a metabolic intermediate, a cell-surface protein mediating membrane transport of ions, a glycoprotein serving to identify a particular cell to its neighbors, an IgG-class antibody circulating in the plasma, an oligonucleotide sequence of DNA in the nucleus, or the like. The various molecules which receptors selectively bind are known as ligands.

Many assays are available for measuring the binding affinity of known receptors and ligands, but the information which can be gained from such experiments is often limited by the number and type of ligands which are available. Novel ligands are sometimes discovered by chance or by application of new techniques for the elucidation of molecular structure, including x-ray crystallographic analysis and recombinant genetic techniques for proteins.

Small peptides are an exemplary system for exploring the relationship between structure and function in biology. A peptide is a sequence of amino acids. When the twenty naturally occurring amino acids are condensed into polymeric molecules they form a wide variety of three-dimensional configurations, each resulting from a particular amino acid sequence and solvent condition. The number of possible pentapeptides of the 20 naturally occurring amino acids, for example, is $20^5$ or 3.2 million different peptides. The likelihood that molecules of this size might be useful in receptor-binding studies is supported by epitope analysis studies showing that some antibodies recognize sequences as short as a few amino acids with high specificity. Furthermore, the average molecular weight of amino acids puts small peptides in the size range of many currently useful pharmaceutical products. Of course, larger peptides may be necessary for many purposes; and polypeptides having changes in only a small number of residues may also be useful for such purposes the analysis of structure-activity relationships.

Pharmaceutical drug discovery is one type of research which relies on such a study of structure-activity relationships. In most cases contemporary pharmaceutical research can be described as the process of discovering novel ligands with desirable patterns of specificity for biologically important receptors. Another example is research to discover new compounds for use in agriculture, such as pesticides and herbicides.

Prior methods of preparing large numbers of different oligomers have been painstakingly slow when used at a scale sufficient to permit effective rational or random screening. For example, the "Merrifield" method (*J. Am. Chem. Soc.* (1963) 85:2149–2154, which is incorporated herein by reference) has been used to synthesize peptides on a solid support. In the Merrifield method, an amino acid is covalently bonded to a support made of an insoluble polymer. Another amino acid with an alpha protected group is reacted with the covalently bonded amino acid to form a dipeptide. After washing, the protective group is removed and a third amino acid with an alpha protective group is added to the dipeptide. This process is continued until a peptide of a desired length and sequence is obtained. Using the Merrifield method, it is not economically practical to synthesize more than a handful of peptide sequences in a day.

To synthesize larger numbers of oligomer sequences, it has also been proposed to use a series of reaction vessels for oligomer synthesis. For example, a tubular reactor system may be used to synthesize a linear oligomer on a solid phase support by automated sequential addition of reagents. This method still does not enable the synthesis of a sufficiently large number of oligomer sequences for effective economical screening.

Methods of preparing a plurality of oligomer sequences are also known in which a foraminous container encloses a known quantity of reactive solid supports, the solid supports being larger in size than openings of the container. The containers may be selectively reacted with desired materials to synthesize desired sequences of product molecules. As with other methods known in the art, this method cannot practically be used to synthesize a sufficient variety of polypeptides for effective screening.

Other techniques have also been described. These methods include the synthesis of peptides on 96 plastic pins which fit the format of standard microtiter plates. Unfortunately, while these techniques have been somewhat useful, substantial problems remain. For example, these methods continue to be limited in the diversity of sequences which can be economically synthesized and screened.

From the above, it is seen that an improved method and apparatus for synthesizing a diverse collection of chemical sequences is desired.

SUMMARY OF THE INVENTION

The present invention provides a general stochastic method for synthesizing random oligomers on solid supports, or particles. The oligomers are composed of a sequence of monomers, the monomers being any member of the set of molecules which can be joined together to form an oligomer or polymer, i.e. amino acids, nucleic acids, carbohydrates, lipids, polyesters, and the like. The method involves producing a large library of solid supports, each support having attached a single oligomer sequence, the oligomers being synthesized in a random combinatorial ("stochastic") fashion. The library is then screened to isolate individual solid supports carrying oligomers that bind to a receptor. Each oligomer sequence in the library is unique, in a preferred embodiment. In another preferred embodiment, the solid supports are nonporous beads. The solid supports may be composed of a single particle, or two or more linked particles.

A further embodiment of the invention is the use of an identifier tag to identify the sequence of monomers in the oligomer. The identifier tag, which may be attached to the same particle as the oligomer or to a second particle attached to the oligomer-carrying particle, may be any recognizable feature that in some way carries the required information, and that is decipherable at the level of one or a few solid supports. The solid supports may be joined to the oligomers and the identifier tag by means of a linker molecule.

In a preferred embodiment, the identifier tag will be an oligonucleotide, preferably composed of pyrimidines. The oligonucleotide identifier tag may contain a 5' and a 3' amplification site, to allow amplification of the tag by, for example, polymerase chain reaction. A DNA sequencing primer site, which may be specific for each step of the oligomer synthesis, may also be included in the oligonucleotide tag. The tag may be designed to include, in the oligonucleotide sequence, information allowing identification of the monomer associated with the addition of the particular tag. The oligonucleotide will be about 100 nucleotides in length, in a preferred embodiment.

DESCRIPTION OF THE SPECIFIC EMBODIMENTS

Figure 1:
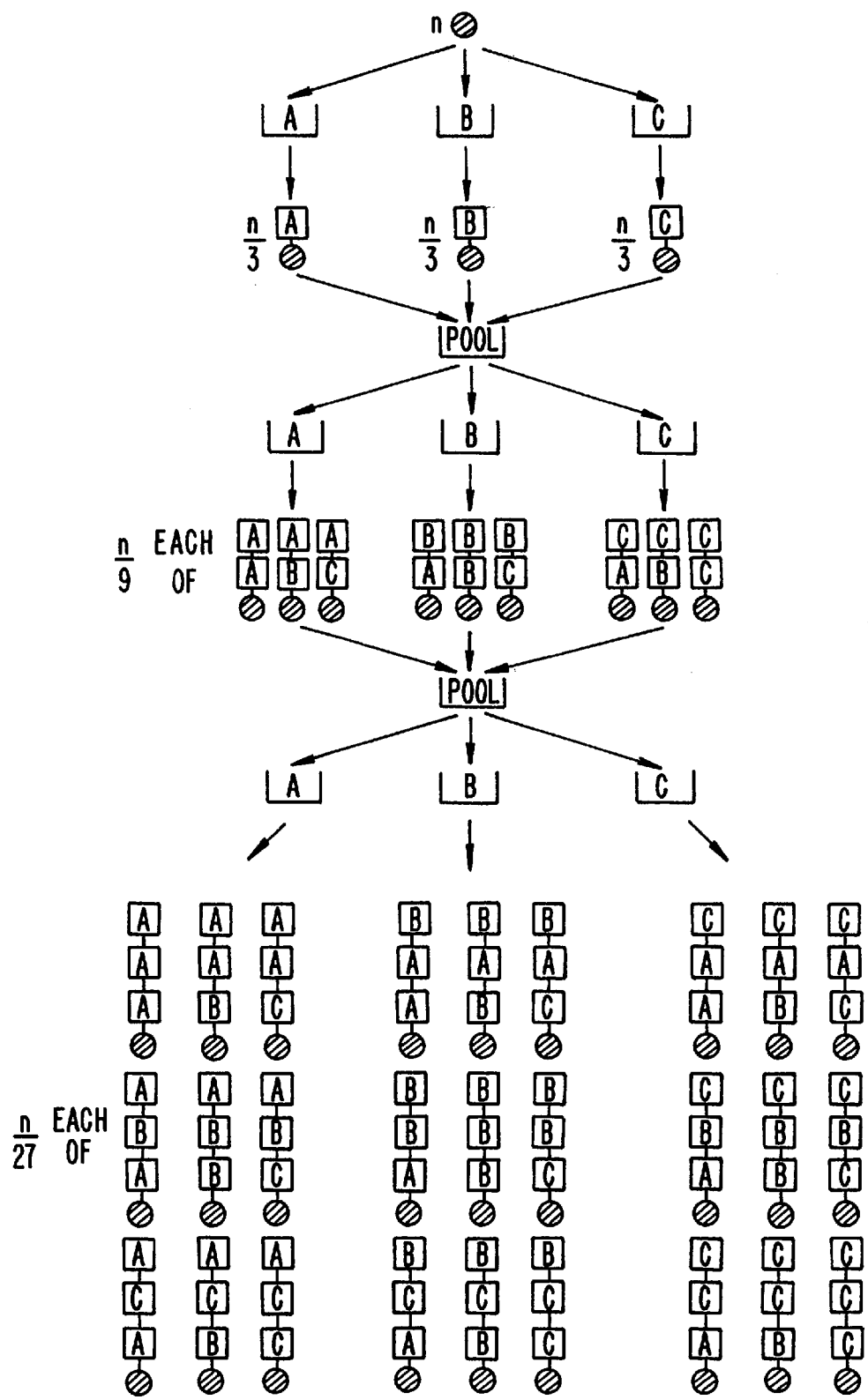
FIG. 1 is a schematic representation of combinatorial oligomer synthesis on particles.

The present invention provides novel methods and instruments for producing large synthetic oligomer libraries. In a preferred embodiment of the present invention, each member of such a library has a means for uniquely identifying the sequence of each oligomer. Methods for screening such libraries and reagents useful for their production are also provided.

Glossary

The following terms are intended to have the following general meanings as they are used herein:

Complementary or substantially complementary: Refers to base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably at least about 98 to 99.5%.

Alternatively, substantial complementarity exists when an RNA or DNA strand will hybridize under selective hybridization conditions to its complement. Typically, selective hybridization will occur when there is at least about 55% identity over a stretch of at least 14 to 25 nucleotides, preferably at least about 65%, more preferably at least about 75%, and most preferably at least about 90% identity. See, M. Kanehisa *Nucleic Acids Res.* 12:203 (1984), incorporated herein by reference.

Stringent hybridization conditions will typically include salt concentrations of less than about 1 M, more usually less than about 500 mM and preferably less than about 200 mM. The hybridization temperature for oligomers will typically be greater than 22° C., more typically greater than about 30° C., and preferably in excess of about 37° C. Longer fragments may require higher hybridization temperatures for specific hybridization. As other factors may dramatically affect the stringency of hybridization, including base composition and length of the complementary strands, presence of organic solvents and extent of base mismatching, the combination of parameters is more important than the absolute measure of any one alone.

Epitope: The portion of an antigen molecule which is delineated by the area of interaction with the subclass of receptors known as antibodies.

Identifier tag: A means whereby one can identify which monomer reactions an individual solid support has experienced in the synthesis of an oligomer. The identifier tag also records the step in the synthesis series in which the solid support visited that monomer reaction. The identifier tag may be any recognizable feature which is, for example: microscopically distinguishable in shape, size, color, optical density, etc.; differently absorbing or emitting of light; chemically reactive; magnetically or electronically encoded; or in some other way distinctively marked with the required information, and decipherable at the level of one (or few) solid support(s). A preferred example of such an identifier tag is an oligonucleotide sequence.

Ligand: A ligand is a molecule that is recognized by a particular receptor. The agent bound by or reacting with a receptor is called a "ligand", a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, proteins, and monoclonal antibodies.

Monomer: Any member of the set of molecules which can be joined together to form an oligomer or polymer. The set of monomers useful in the present invention includes, but is not restricted to, for the example of peptide synthesis, the set of L-amino acids, D-amino acids, or synthetic amino acids. As used herein, monomers refers to any member of a basis set for synthesis of an oligomer. For example, dimers of L-amino acids form a basis set of 400 monomers for synthesis of polypeptides. Different basis sets of monomers may be used at successive steps in the synthesis of a polymer.

Oligomer or Polymer: The oligomer or polymer sequences of the present invention are formed from the chemical or enzymatic addition of monomer subunits. Such oligomers include, for example, both linear, cyclic, and branched polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be readily apparent to one skilled in the art upon review of this disclosure.

Peptide: A peptide is an oligomer in which the monomers are alpha amino acids and which are joined together through amide bonds and alternatively referred to as a polypeptide. In the context of this specification it should be appreciated that the amino acids may be the L-optical isomer or the D-optical isomer. Peptides are more than two amino acid monomers long, and often more than 20 amino acid monomers long. Standard abbreviations for amino acids are used (e.g., P for proline). These abbreviations are included in Stryer, *Biochemistry*, Third Ed., 1988, which is incorporated herein by reference.

Oligonucleotides: An oligonucleotide is a single-stranded DNA or RNA molecule, typically prepared by synthetic means. Those oligonucleotides employed in the present invention will be 50 to 150 nucleotides in length, preferably from 80 to 120 nucleotides, and most preferably about 100 nucleotides, although oligonucleotides of different length may be appropriate. Suitable oligonucleotides may be prepared by the phosphoramidite method described by Beaucage and Carruthers, *Tetra. Letts.* 22:1859–1862 (1981), or by the triester method according to Matteucci, et al., *J. Am. Chem. Soc.*, 103:3185 (1981), both incorporated herein by reference, or by other methods such as commercial automated oligonucleotide synthesizers.

Operably linked: A nucleic acid is operably linked when it is placed into a functional relationship with another nucleic acid sequence. For instance, a promoter or enhancer is operably linked to a coding sequence if it affects the transcription of the sequence. Generally, operably linked means that the DNA sequences being linked are contiguous and, where necessary to join two protein coding regions, contiguous and in reading frame.

Receptor: A molecule that has an affinity for a given ligand. Receptors may be naturally-occurring or manmade molecules. Also, they can be employed in their unaltered natural or isolated state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "ligand-receptor pair" is formed when two macromolecules have combined through molecular recognition to form a complex.

Other examples of receptors which can be investigated by this invention include but are not restricted to:

a) Microorganism receptors: Determination of ligands that bind to receptors, such as specific transport proteins or enzymes essential to survival of microorganisms, is useful in a new class of antibiotics. Of particular value would be antibiotics against opportunistic fungi, protozoa, and those bacteria resistant to the antibiotics in current use.

b) Enzymes: For instance, the binding site of enzymes such as the enzymes responsible for cleaving neurotransmitters. Determination of ligands that bind to certain receptors, and thus modulate the action of the enzymes that cleave the different neurotransmitters, is useful in the development of drugs that can be used in the treatment of disorders of neurotransmission.

c) Antibodies: For instance, the invention may be useful in investigating the ligand-binding site on the antibody molecule which combines with the epitope of an antigen of interest. Determining a sequence that mimics an antigenic epitope may lead to the development of vaccines of which the immunogen is based on one or more of such sequences, or lead to the development of related diagnostic agents or compounds useful in therapeutic treatments such as for autoimmune diseases (e.g., by blocking the binding of the "self" antibodies).

d) Nucleic Acids: The invention may be useful in investigating sequences of nucleic acids acting as binding sites for cellular proteins ("trans-acting factors"). Such sequences may include, e.g., enhancers or promoter sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides are described in, Lerner, R. A., et al., *Science* 252: 659 (1991), which is incorporated herein by reference.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone that can only be obtained from cadavers or by recombinant DNA technology. Other examples are the vasoconstrictive hormone receptors; determination of those ligands that bind to a receptor may lead to the development of drugs to control blood pressure.

g) Opiate receptors: Determination of ligands that bind to the opiate receptors in the brain is useful in the development of less-addictive replacements for morphine and related drugs.

Substrate or Solid Support: A material having a rigid or semi-rigid surface. Such materials will preferably take the form of small beads, pellets, disks or other convenient forms, although other forms may be used. In some embodiments, at least one surface of the substrate will be substantially flat. A roughly spherical shape is preferred.

Synthetic: Produced by in vitro chemical or enzymatic synthesis. The synthetic libraries of the present invention may be contrasted with those in viral or plasmid vectors, for instance, which may be propagated in bacterial, yeast, or other living hosts.

Methods for Producing Large Synthetic Oligomer Libraries

A general method of random oligomer synthesis is provided that produces the enormous numbers of compounds available with recombinant systems and the monomer set diversity available with chemical synthesis methods. By means of the present method it is possible to readily produce up to $10^{12}$ different oligomers, a dramatic improvement over previous methods. It also provides a facile means of oligomer identification. The general method comprises:

(a) Producing a large, highly diverse collection or library, each member of such a library comprising solid supports having attached a single oligomer sequence (e.g., a peptide). The solid support is attached to the oligomer by means of a linker that has an appropriate functional group at each end, one group appropriate for attachment to the support and the other group appropriate for attachment to the oligomer. Such a collection may contain, for example, all combinations of n monomers assembled into X length oligomers ($n^X$=up to $10^8$ to $10^{12}$ compounds). In one embodiment, n will be 5 or 6, and the collection will contain about $10^5$ or $10^6$ different members, respectively. It may also contain oligomers having different monomer units at, for example, only one or a small number of positions while having an identical sequence at all other positions;

(b) Synthesizing the oligomers in a random combinatorial ("stochastic") fashion by chemical and/or enzymatic assembly of monomer units;

(c) Screening the collection to isolate individual solid supports carrying oligomers active in binding to a receptor.

A synthetic oligomer library may be produced by synthesizing on each of a plurality of solid supports a single oligomer sequence, the oligomer sequence being different for different solid supports. The oligomer sequence is synthesized in a process comprising the steps of:

a) apportioning the supports in a stochastic manner among a plurality of reaction vessels;

b) exposing the supports in each reaction vessel to a first monomer;

c) pooling the supports;

d) apportioning the supports in a stochastic manner among the plurality of reaction vessels;

e) exposing the supports in each reaction vessel to a second monomer; and f) repeating steps a) through e) from at least one to twenty times.

Typically, substantially equal numbers of solid supports will be apportioned to each reaction vessel. In one embodiment of the method, the monomers are chosen from the set of amino acids and the resulting oligomer is a peptide.

In a preferred embodiment of the invention, the solid supports on which the oligomers are synthesized also have attached an identifier tag that can be easily decoded to report the sequence of the oligomer contained on each solid support. The identifier tags may be attached to the solid support by means of a linker that has an appropriate functional group at each end, one group appropriate for attachment to the support and the other group appropriate for attachment to the identifier tag. It will be readily appreciated after reading the disclosure below that one could also produce large synthetic oligomer libraries lacking identifier tags.

A synthetic oligomer library that incorporates identifier tags is produced by synthesizing on each of a plurality of solid supports a single oligomer sequence and one or more identifier tags identifying the oligomer sequence. The oligomer sequence and identifier tags are synthesized in a process comprising the steps of:

a) apportioning the supports among a plurality of reaction vessels;

b) exposing the supports in each reaction vessel to a first oligomer monomer and to a first identifier tag monomer;

c) pooling the supports;

d) apportioning the supports among a plurality of reaction vessels; and e) exposing the supports to a second oligomer monomer and to a second identifier tag monomer.

In one embodiment, the steps of this process will be repeated one to about 20 times.

Alternatively to exposing the solid supports to a oligomer monomer and an identifier tag monomer at the same time, the supports may be exposed sequentially to the first oligomer monomer and then to the first identifier tag monomer. The supports are then pooled and exposed to the second oligomer monomer and then to the second identifier tag monomer. These steps are then repeated, typically from one to about 20 times.

The invention is described herein primarily with regard to the preparation of molecules containing sequences of amino acids, but could readily be applied in the preparation of other oligomers, as can be appreciated by those skilled in the art.

There are various solid supports useful in preparation of the synthetic oligomer libraries of the present invention. It is understood that such solid supports are solid phase supports commonly used for solid phase synthesis of, for example, such oligomers as enumerated above, and thus are well known to those skilled in the art. In some embodiments of the present invention, such solid supports have novel features as described below.

The chemical or enzymatic synthesis of the oligomer libraries of the present invention takes place on such solid supports. The term "solid support" as used herein embraces a particle with appropriate sites for oligomer synthesis and, in some embodiments, tag attachment and/or synthesis, or it may be a more massive solid support of up to 1 mm in size. In general, the solid support size is in the range of 1 nm to 100 μm. Such solid supports may be of any shape, although they will preferably be roughly spherical. Such solid supports may consist of many materials, limited primarily by capacity for derivatization to attach any of a number of chemically reactive groups, and compatibility with the chemistry of oligomer synthesis and tag attachment. They need not necessarily be homogenous in size, shape, or composition; though usually will be somewhat uniform. Two or more distinctly different populations of solid supports may be used for certain purposes. Except as otherwise noted, the chemically reactive groups with which such solid supports may be derivatized are those commonly used for solid state synthesis of the respective oligomer and thus will be well known to those skilled in the art.

It should be noted that the solid supports of the present invention, as defined above, would not include such things as living cells, viruses, or cloning vectors such as phage vectors or plasmids.

An Illustration of the Method

As a specific example of the method, one may consider the synthesis on resin beads of peptides three residues in length, assembled from a monomer set of three different monomer reaction components: A, B, and C. The first monomer is coupled to beads, and the beads from all the reactions are then pooled (see, FIG. 1). The pool now contains approximately equal numbers of solid supports with each of the three monomers in the first residue position. The pool is mixed and redistributed to the separate monomer reaction tubes or vessels containing A, B, or C as the monomer. The second residue is coupled. Following this reaction, each tube now has beads with three different monomers in position one and the monomer contained in each particular second reaction tube in position 2. All reactions are pooled again, producing a mixture of beads each bearing one of the nine possible dimers. The pool is again distributed among the three reaction vessels, coupled, and pooled. This process of sequential synthesis and shuffling yields beads that have passed through all the possible reaction pathways and display all trimers of three amino acids ($3^3$=27). Thus, a complete set of the trimers of A, B, and C is constructed. As can be readily appreciated, the use of a sufficiently large number of synthesis beads helps to ensure that the set completely represents the various combinations of monomers employed in this random, combinatorial synthesis scheme.

The mixture of trimers can be screened for binding to receptors by methods described below.

Oligomer Synthesis

This method of assembling oligomers from many types of subunits requires using the appropriate coupling chemistry for a given set of monomer units or building blocks. Any set of building blocks that can be attached to one another in a step-by-step fashion can serve as the monomer set. The attachment may be mediated by chemical, enzymatic, or other means, or by a combination of these. The resulting oligomers can be linear, cyclic, branched, or assume various other conformations as will be apparent to those skilled in the art. For example, techniques for solid state synthesis of polypeptides are described, for example, in Merrifield, *J. Amer. Chem. Soc.* 85:2149–2156 (1963). Peptide coupling chemistry is also described in *The Peptides*, Vol. 1, (eds. Gross, E., and J. Meienhofer), Academic Press, Orlando (1979), which is incorporated herein by reference).

To synthesize the oligomers, a large number of the solid supports are apportioned among a number of reaction vessels. In each reaction, a different monomer is coupled to the growing oligomer chain. The monomers may be of any type that can be appropriately activated for chemical coupling, or any type that will be accepted for enzymatic coupling. Because the reactions may be contained in separate reaction vessels, even monomers with different coupling chemistries can be used to assemble the oligomers (see, *The Peptides*, op. cit). The coupling time for some of the monomer sets may be long. For this reason the preferred arrangement is one in which the monomer reactions are carried out in parallel. After each coupling step, the solid supports on which are synthesized the oligomers of the library are pooled and mixed prior to re-allocation to the individual vessels for the next coupling step. This shuffling process produces solid supports with many oligomer sequence combinations. If each synthesis step has high coupling efficiency, substantially all the oligomers on a single solid support have the same sequence. That sequence is determined by the synthesis pathway (monomer reactions and the order of reactions experienced by the solid supports) for any given solid support. The maximum length of the oligomers is about 20, preferably from 3 to 8 residues in length, and in some cases a length of 10 to 12 residues is preferred. Protective groups known to those skilled in the art may be used to prevent spurious coupling (see, *The Peptides*, Vol. 3, (eds. Gross, E., and J. Meienhofer), Academic Press, Orlando (1981), which is incorporated herein by reference)

Modifications of this completely random approach are also possible. For example, the monomer set may be expanded or contracted from step to step; or, in principle, the monomer set could be changed completely for the next step (e.g., amino acids in one step, carbohydrates in the next) if the coupling chemistry were available (see, Gait, M. J., *Oligonucleotide Synthesis: A Practical Approach*, IRL Press, Oxford (1984), Friesen, R. W. and S. J. Danishefsky, *J. Amer. Chem. Soc.*, 111:6656 (1989), and Paulsen, H. *Angew. Chem. Int. Ed. Engl.*, 25:212 (1986), all of which are incorporated herein by reference). A monomer unit for peptide synthesis, for example, may include single amino acids or larger peptide units, or both. One variation is to form several pools of various sequences on solid supports to be distributed among different monomer sets at certain steps of the synthesis. It is clear that, by this approach, one can also build oligomers of different lengths with either related or unrelated sequences, and fix certain monomer residues at some positions while varying the other residues, to construct oligomer frameworks wherein certain residues or regions are altered to provide diversity.

With enough solid supports and efficient coupling it is possible to generate complete sets of certain oligomers, if desired. The appropriate size of the solid supports depends on (1) the number of oligomer synthesis sites and identifier tag attachment sites desired; (2) the number of different compounds to be synthesized (and the number of solid supports bearing each oligomer that are needed for screening); and (3) the effect of the size of the solid supports on the specific screening strategies [e.g. fluorescence-activated cell sorters (FACS)] to be used.

As a specific example, solid supports of 1 $\mu$m in diameter may be used. If each reaction contains approximately 0.2 ml of solid supports, and the oligomers are synthesized from a set of 50 monomers (50 parallel reactions), then a total of 10 ml of solid supports, or approximately $10^{13}$ solid supports would be required. If one wishes to make hexamers with these 50 monomers, there are $1.5 \times 10^{10}$ possible sequences, and each specific sequence would be represented on about $10^3$ solid supports. It is estimated that the capacity of each bead, based on the capacity of commonly used peptide synthesizing resins, is about 0.1 pg of peptide per solid support. By this estimation, then, each solid support would have about 100 amol or $10^8$ oligomer chains.

To improve washing efficiencies, solid supports less porous than typical peptide synthesis resins are preferable. These will have a lower density of growing chains, but even with a decrease in capacity of several orders of magnitude, sufficient oligomer densities can be produced for efficient screening. With the less porous supports, a greater proportion of the peptides will be accessible for binding to the receptor during the screening process. Also, the less porous supports will reduce the carryover of tags from one reaction to the next, thus improving the accuracy of reading the dominant (correct) tags. Suitable support materials include glass, latex, heavily cross-linked polystyrene or similar polymers, gold or other colloidal metal particles, and other materials known to those skilled in the art.

Identifying the Sequence of the Oligomers Displayed on a Solid Support

The oligomer sequences on each recovered solid support must then be identified. It may not be possible, in some cases, to directly determine the composition of the oligomers on a single solid support. The present invention provides a method for identifying the oligomer composition and the sequence of the oligomer on any given solid support.

Figure 2:
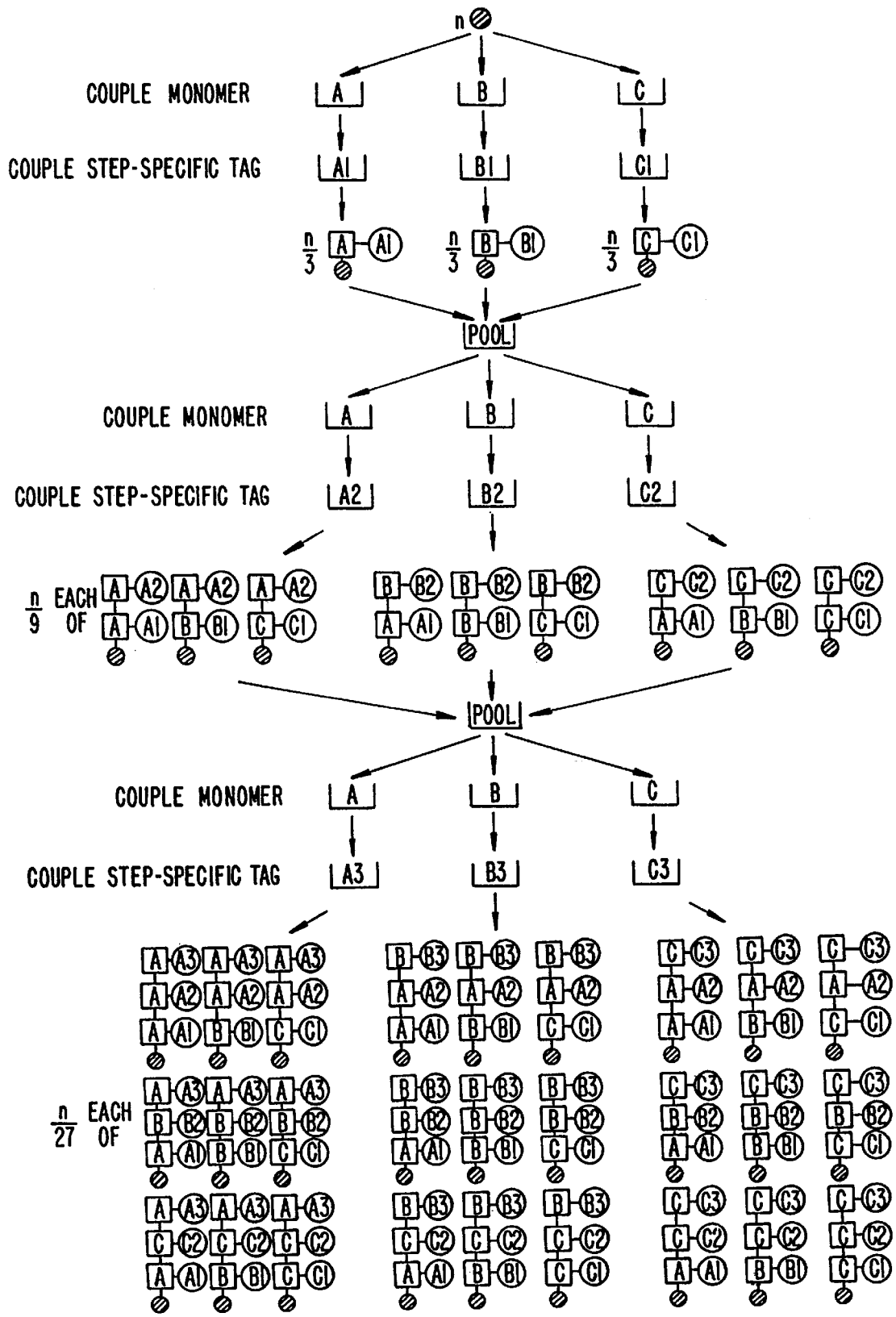
FIG. 2 is a schematic representation of concurrent combinatorial oligomer synthesis and particle tagging.
Figure 3A:
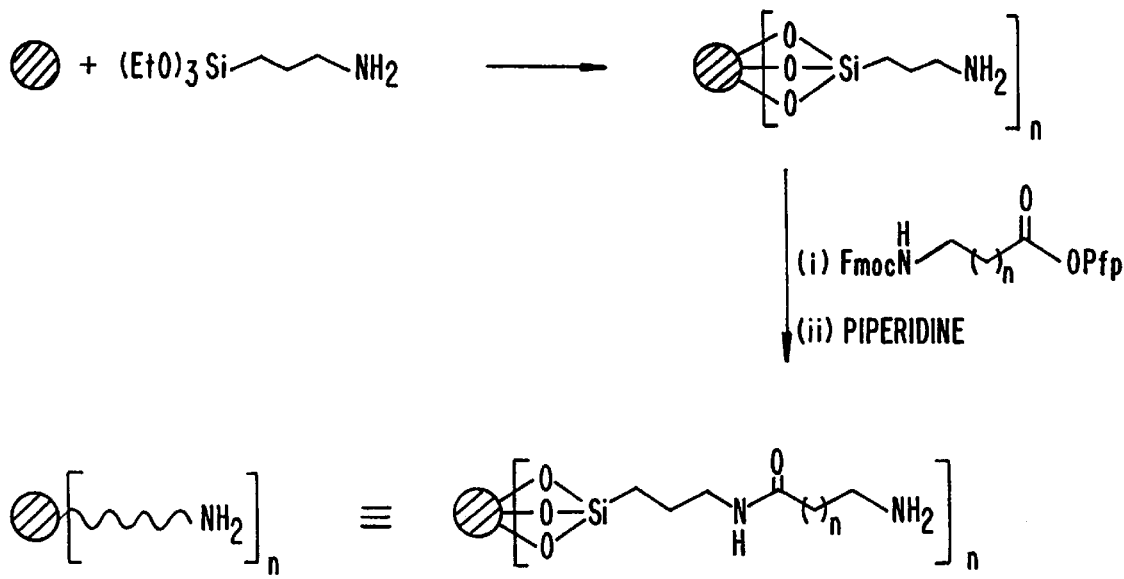
FIGS. 3A–3F are a description of one method of bead functionalization, the compatible chemistries for peptide synthesis and round by round attachment of oligonucleotide identifier tags, including synthesis of amino-functionalized beads, shown in FIG. 3A the structure of protected 5' maleimidyl oligonucleotides, shown in FIG. 3B amino acid coupling and introduction of a thiol "handle," shown in FIG. 3C step-specific oligonucleotide attachment to a bead, shown in FIG. 3D subsequent amino acid coupling(s) and oligonucleotide attachment(s), shown in FIG. 3E and peptide and oligonucleotide deprotection, shown in FIG. 3F.
Figure 3B:
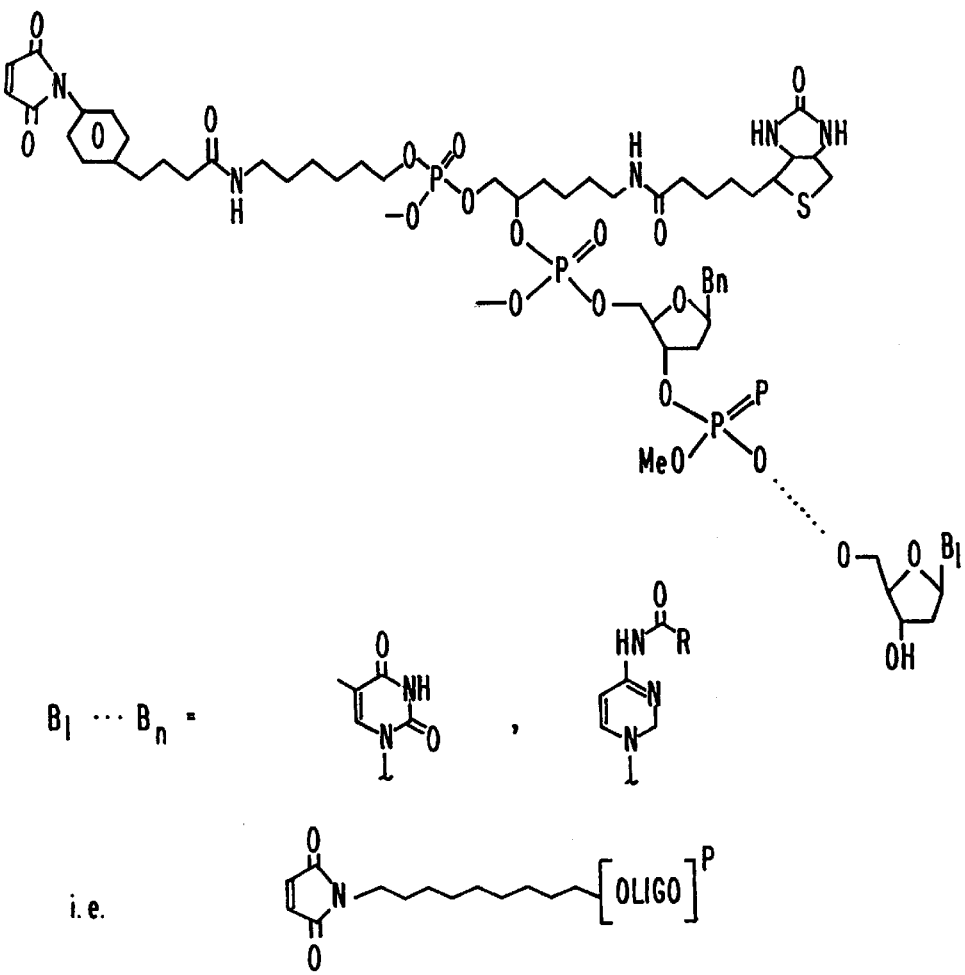
Figure 3C:
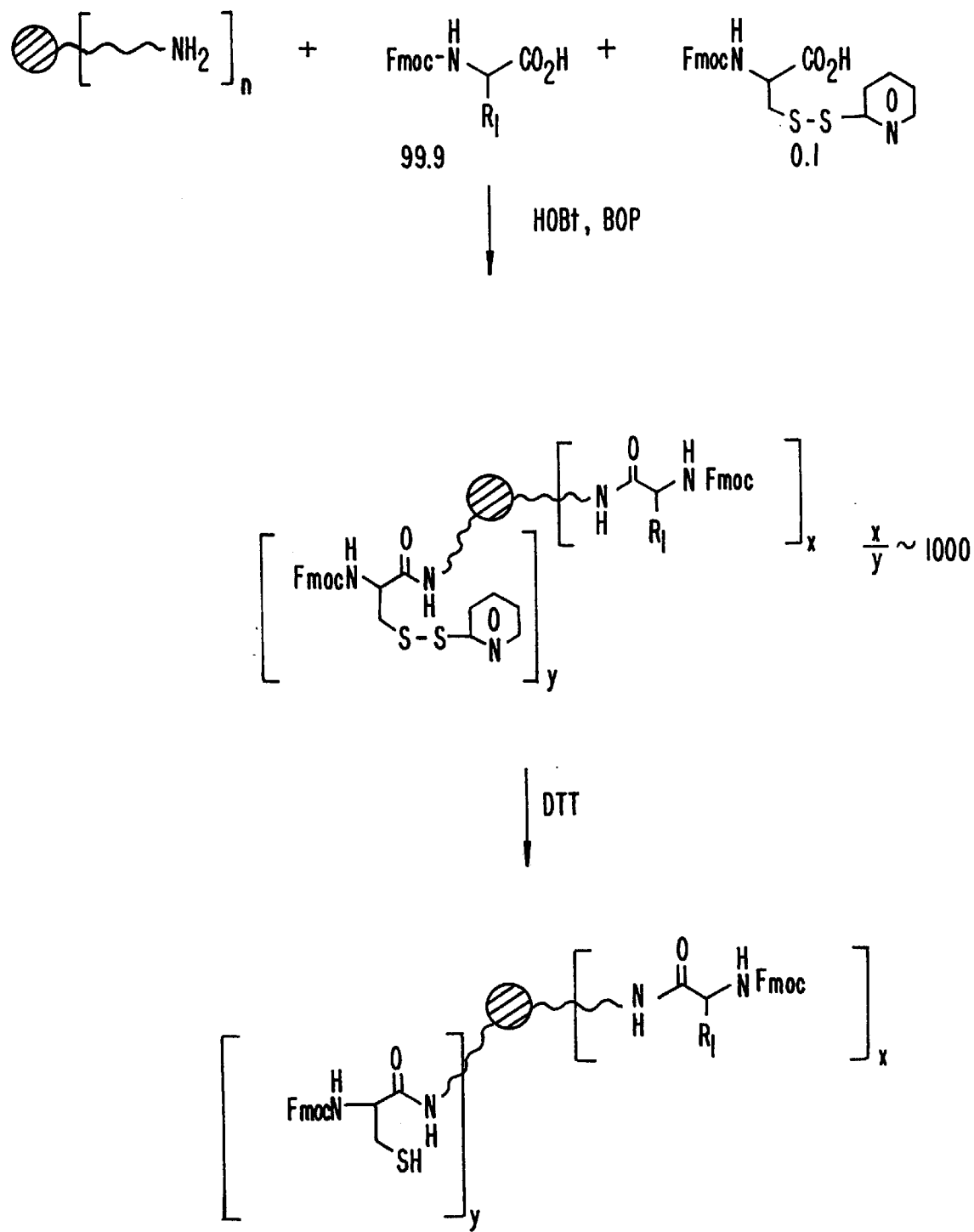
Figure 3D:
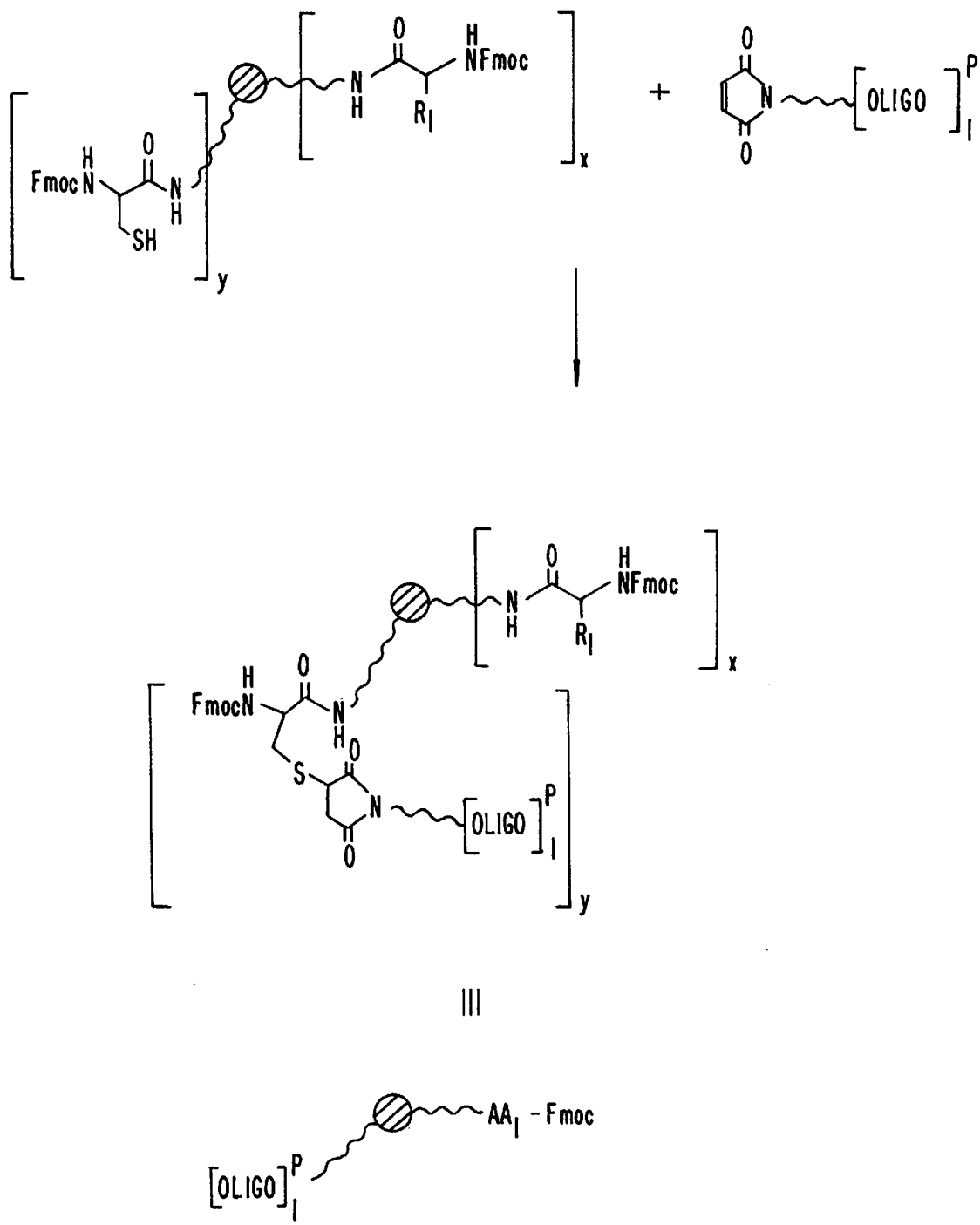
Figure 3E:
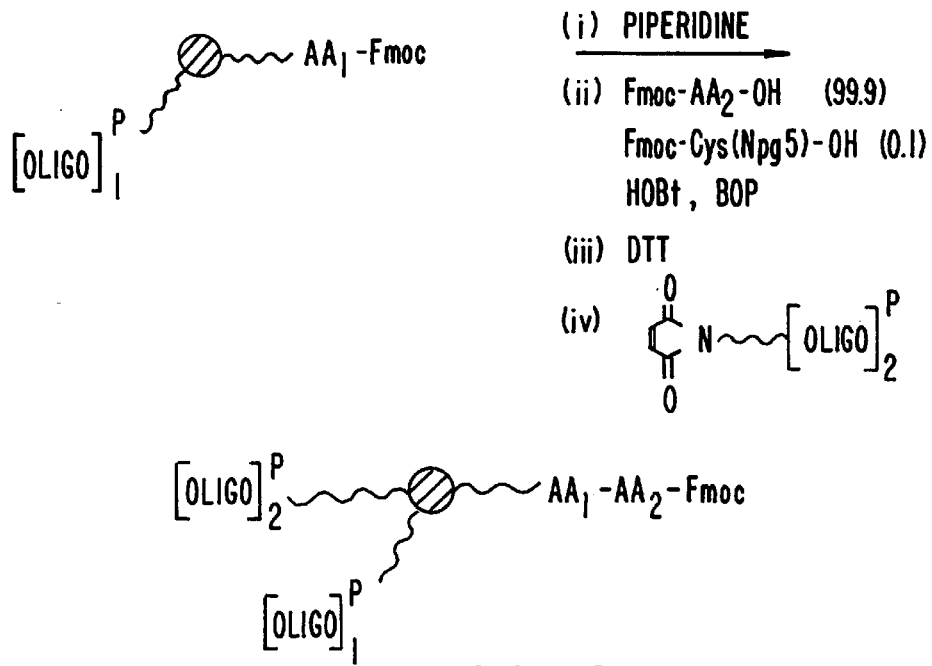
Figure 3F:
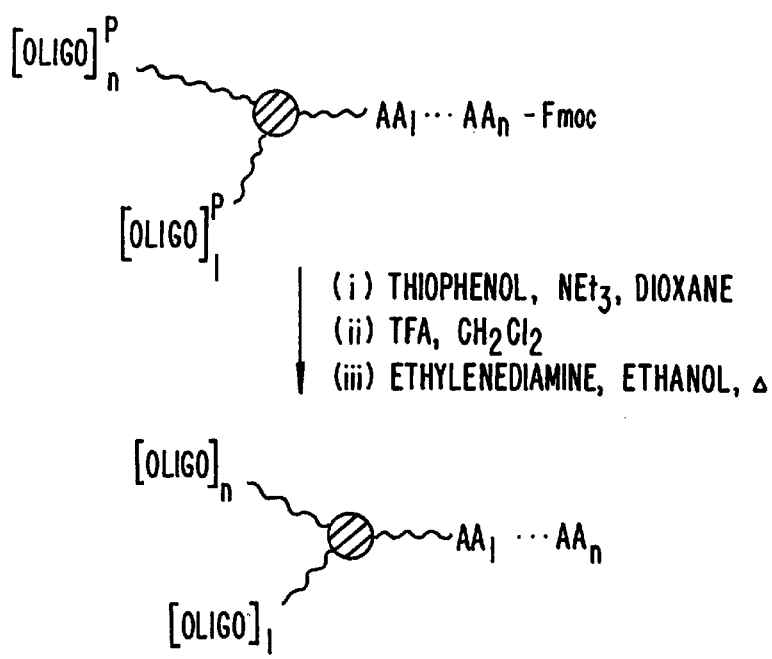

By tracking the synthesis pathway that each solid support has taken, however, it is possible to deduce the oligomer sequence on any support. The method involves the attachment to each solid support (a resin bead, for example) of an identifier tag that indicates which monomer reaction that bead has visited, and that also indicates the particular step number of the visit. After a series of synthesis steps (and concurrent identifier tag addition), "reading" the set of identifier tags attached to a bead reveals the sequence of the oligomer synthesized on that bead. For example, one might attach microscopically recognizable, alphanumeric tags to each bead (see FIG. 2): "A1" would indicate that the bead participated in the A-monomer reaction at step 1, "B3" would mean B-monomer was added in step 3, and so on. At the end of the 3-step synthesis, the bead would have three tags attached. These might be A1, C2, B3 indicating that the sequence of the peptides on the bead is (C to N-terminal) ACB. It is evident that this scheme requires a number of distinct identifier tags equal to the product of the number of different monomers and the number of synthesis steps (this product being nine in the present example). The number of identifier tags is reduced if the symbols are attached to one another in the order of the steps: A, A-C, A-C-B. In this case only as many identifier tags are needed as monomers. A means of building the identifier tag in much the same way as the peptides are built is also needed, so as to preserve a record of what was monomer was added, and in which addition step.

The identifier tags therefore identify each monomer reaction that an individual solid support has experienced, and records the step in the synthesis series in which the solid support visited that monomer reaction. The tags may be attached to all (or most) of the solid supports in each synthesis reaction immediately before, during, or immediately after the monomer addition reaction, whatever is the most convenient and compatible with the type of identifier tag, its mode of attachment, and the chemistry in use for oligomer synthesis. Clearly, the identifier tag must be added when the solid supports that have undergone a specific monomer addition step are still physically together and can be tagged as a group.

In some cases, of course, when only a small number of monomer units of an oligomer are varied, it will be necessary to identify only those monomers which vary among the oligomers. This will be the case, for example, if one wishes to vary only five amino acids in a peptide 50 amino acids in length. One may uniquely identify the sequence of each peptide by providing for each solid support an identifier tag specifying only the five amino acids varied in each sequence, as will be readily appreciated by those skilled in the art.

In such cases it will also be appreciated that all solid supports may remain in the same reaction vessel for the addition of monomer units that all solid supports bear in common, and may be apportioned among different reaction vessels for the addition of monomer units which distinguish each solid support.

The identifier tag may be any recognizable feature that is, for example: microscopically distinguishable in shape, size, color, optical density, etc.; differently absorbing or emitting of light; chemically reactive; magnetically or electronically encoded; or in some other way distinctively marked with the required information, and decipherable at the level of one (or few) solid supports.

One can construct such microscopically identifiable tags as small beads of recognizably different sizes, shapes, or colors, or as bar codes, inter alia. The identifier tag can also be an encodable molecular structure. The best example of this is a nucleic acid sequence, i.e., RNA or DNA assembled from natural or modified bases. Synthetic oligodeoxyribonucleotides, however, are the preferred information-bearing identifier tag.

Oligonucleotide identifier tags: Oligonucleotides are a natural, high density information storage medium. The identity of monomer type and the step of addition is easily encoded in a short oligonucleotide sequence and attached, for example, to each peptide synthesis bead. When a single bead is isolated by screening, e.g., for receptor binding, the attached oligonucleotides can be amplified by PCR (See, e.g., *PCR Protocols: A Guide to Methods and Applications.* (Innis, M, Gelfand, D., Sninsky, J. and White, T., eds.), Academic Press, San Diego (1990), which is incorporated herein by reference), or by other nucleic acid amplification techniques, such as the ligase chain reaction or the self-sustained sequence replication system, and easily sequenced to decode the identity of the peptide on the bead. For this purpose, one can use any of a variety of sequencing methods, including sequencing by sequence-specific probe hybridization.

There are several ways that oligonucleotides can be used as identifier tags. Some examples are:

(1) They may be assembled base-by-base before, during, or after the corresponding oligomer (e.g., peptide) synthesis step. In this case of base-by-base synthesis, the tag for each step is a single nucleotide. This strategy has the advantage of preserving the order of the steps in the linear array of the oligonucleotide chain as it grows in parallel with the oligomer. In order to preserve the chemical compatibility of the parallel synthetic steps (oligonucleotides and peptides, for example), it may be necessary in some cases to modify the standard synthesis chemistries.

(2) A variation of base-by-base assembly is the block-by-block approach, whereby encoded blocks of 3 to 10 or more bases are added as protected, activated blocks. Each block carries the monomer-type information, and the order of addition represents the order of the monomer addition reaction. This has advantages and disadvantages similar to (1) above.

(3) Fully formed protected oligonucleotides containing (PCR) amplification primer sites, monomer-specific information, and order-of-reaction information, and that are 50 to 150 bases in length, may be added at each step. These are coupled to chemically reactive locations on each solid support. At the end of a series of n oligomer synthesis steps, there would be n differently encoded sets of oligonucleotide identifier tags on each solid support. After identifying the solid supports carrying oligomers with ligand activity, the oligonucleotides on the solid support are amplified by PCR and sequenced to decode the identity of the oligomer also carried by the solid support.

Attaching the Oligonucleotide Identifier Tags to the Synthesis Particles

The identifier tags may be attached to chemically reactive groups (unmasked thiols or amines, for example) on the surface of a synthesis support functionalized to allow synthesis of an oligomer and attachment or synthesis of the oligonucleotide identifier tag; or to monomers that are incorporated into a small proportion of the oligomer chains; or as caps on a small number of the oligomer chains.

In one embodiment, the solid supports will have chemically reactive groups that are protected using two different types of protecting groups. The solid supports will then be exposed to a first activator, removing the first type of solid support from, for example, the chemically reactive groups that serve as oligomer synthesis sites. After reaction with the first monomer, the solid supports will then be exposed to a second activator which removes the second type of protecting group, exposing, for example, the chemically reactive groups that serve as identifier tag attachment sites. One or both of the activators may be in a solution that is contacted with the supports. The first activator may be in a solution that also contains the first monomer; similarly, the second activator may be in the same solution as the second monomer.

When activators are incorporated into the method of preparing a synthetic peptide library having a plurality of different members, each member comprising a solid support attached to a different single peptide sequence and an oligonucleotide identifier tag identifying said peptide sequence, the method may have the steps of:

a) apportioning the solid supports among a plurality of reaction vessels;

b) reacting the solid supports with a solution in each reaction vessel comprising (1) a first activator to remove a first protective group from the solid support, (2) a first amino acid or peptide; and (3) a first nucleotide or oligonucleotide;

c) pooling the solid supports;

d) apportioning the pooled solid supports among a plurality of reaction vessels; and e) reacting the solid supports with a solution in each reaction vessel comprising (1) a second activator to remove a second protective group from the solid support, (2) a second amino acid or peptide, and (3) to a second nucleotide or oligonucleotide.

Another possible embodiment is the use of two solid supports, such as beads, that are physically linked together, one with synthesis sites (linkers) for the oligomer and one with attachment sites (linkers) for the identifier tags. This arrangement allows the segregation of oligomers and identifier tags into discrete "zones"; and it permits the use of different chemically reactive groups for attachment. The solid supports can be derivatized separately and then linked under conditions where all or nearly all of the synthesis solid supports will have a tag-attachment solid support in tow. The solid supports can be of different sizes, as for example a large synthesis bead with several (or many) smaller tag-attachment beads linked. In one embodiment, the first solid support will have at least one attached amino acid and the second solid support will have at least one attached nucleotide.

The mode of linking the two beads is constrained by the chemistry of oligomer synthesis. The most obvious means of linking the beads is with a heterobifunctional cross-linking agent (for examples of such agents, see *Pierce ImmunoTechnology Catalog and Handbook*, 1991, op. cit., pp. E10–E18) interacting with the dominant chemically reactive groups on each species of solid support.

A description of one method of bead functionalization, the compatible chemistries for peptide synthesis and round by round attachment of oligonucleotide identifier tags is shown in FIGS. 3.1–3.6. Glass beads are derivatized using aminopropyltriethoxysilane and a β-alanine spacer group is coupled using activated ester methodology. Commercially available Fmoc protected amino acids and standard BOP coupling chemistry is employed for the peptide synthesis (see *The Peptides*, Vol.1 and Vol.3, on. cit.). Protected polypyrimidine oligonucleotides (e.g. cytidine protected as $N^4$-Bz-C) are irreversibly attached using maleimide chemistry to readily unmasked thiol groups that are incorporated into the growing peptide chains at low frequency (say 0.1%) as cysteine residues. The oligonucleotide tags incorporate a biotin group to facilitate their purification on a monomeric avidin column (*Pierce ImmunoTechnology Catalog and Handbook*, 1991, which is incorporated herein by reference) and use phosphate protecting groups with greater base stability than the standard β-cyanoethyl group (e.g. O-methyl phosphates). Peptide and oligonucleotide deprotection is effected by sequential treatment with thiophenol, trifluoroacetic acid and ethanolic ethylenediamine at 55 degrees C.

Encoding the Identifier Information—Oligonucleotide Tags As an Example

The choice of bases used in the oligonucleotide identifier tag is dictated by the chemistry of oligomer synthesis. For example, the use of strong acid to deprotect peptides would depurinate nucleic acids. Therefore, when standard chemistries for peptide chemistries are employed, the pyrimidines C and T could be used in a binary code. Thus, in a preferred embodiment, the identifier tag will be an oligopyrimidine sequence.

Figure 4:
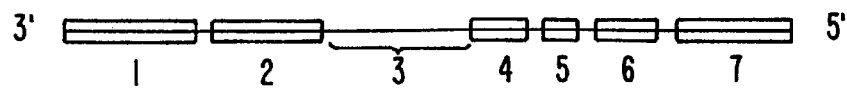
FIG. 4 is a schematic representation of one example of an oligonucleotide tag.

Information retrieval from oligonucleotide identifier tags is possible through various encryption schemes, one of which is described below. For example, as shown in FIG. 4, one may use oligonucleotides of about 100 bases (or somewhat longer), each having seven regions:

Region 1. 3'-PCR primer site (20 to 25 bases). This site is used in conjunction with another PCR site (at the 5'-end of the oligonucleotide) to prime amplification by PCR. (Other amplification methods may also be used, as described below).

Region 2. "Step-specific" DNA sequencing primer site (15–20) bases). This site is specific for the particular numbered step in the synthesis series. All the oligonucleotides added to all the beads at a particular step will have this sequence in common. Each numbered step will have a highly specific primer site representing that step.

Region 3. Spacer (20–30 bases). An spacer segment of variable length, but preferably 20 to 30 bases long, places the coding site sufficiently distant from the sequencing primer site to give a good "read" through the monomer encoding or identification region.

Region 4. Monomer identification region (8 bases). Each base in this string represents one bit of binary code, where, for example, T=0 and C=1. Each set of step-specific identifier tags consists of 8 oligonucleotides with a 1 (C) at one of the 8 positions. These may be thought of as switches set to "on" at the different positions. Each monomer type is encoded by a mixture of 1 to 8 of these "switch" oligonucleotides.

Region 5. Step number confirmation region (4 bases+2 bases on either side for region distinction). Four bits in this short stretch encodes the step number. This is redundant to the sequencing primer, but can be used to confirm that the proper primers were used, and that the right step is decoded.

Region 6. Repeat of the monomer identification region (8 bases). This has the same information as region 4, and is used to confirm monomer identity. Installing this second monomer encoding region also increases the probability that a good sequencing "read" will be obtained.

Region 7. 5'-PCR primer site. (20 to 25 bases). Site for annealing of the second PCR primer for amplification of the sequence.

The length of oligonucleotides with these features will commonly be between 75 and 125 bases.

An 8 bit format can encode 256 different monomer types. The number of steps that can be encoded is determined by the number of step-specific sets (of 8 per set) of oligonucleotides on hand. With 10 sets (80 oligos) one can encode up to 256 different monomers assembled into oligomers up to 10 units long (thus providing encoding capability for up to $256^{10}=1.2\times10^{24}$ oligomer sequences).

The coded identifier tags may be used as follows. Each monomer is assigned a specific binary number (e.g. Ala=00000001, Gly=00000110, etc.). The appropriate oligonucleotides are combined to give the correct binary code.

When specific beads are isolated in a receptor screening experiment, they may be segregated as individual beads by a number of means, including: infinite dilution, micromanipulation, or preferably, fluorescence activated cell sorting (FACS) (actually, in this case, fluorescence activated solid support sorting) (*Methods in Cell Biology*, Vol. 33, (Darzynkiewicz, Z. and Crissman, H. A., eds.), Academic Press; and Dangl, J. L. and L. A. Herzenberg, *J. Immunol. Methods* 52:1–14 (1982), both incorporated herein by reference). The oligonucleotide identifier tags carried by a single solid support are then amplified (e.g., by PCR). If the limit of detection is on the order of 100 molecules, at least 100 (and preferably many more) copies of each oligonucleotide on a bead would be required. Single strands are produced by one of the methods described below and the material is divided into as many separate sequencing reactions as there were oligomer synthesis steps (employing a different sequencing primer for each step tag). The reactions are performed and run on a standard sequencing gel, and the oligomer sequence deduced from the code revealed in the resulting sequence information.

An alternative strategy is to use common PCR primers and common sequencing primers (the sequencing primer may even overlap a PCR primer) and identify the step by hybridization to oligonucleotide probes that are complementary to each step-specific sequence in the oligonucleotides from the bead. A single set of sequencing reactions are performed on all of the amplified oligonucleotides from a single bead, and the reaction products are run in a single set of lanes on a sequencing gel. The reaction products are then transferred to a suitable hybridization membrane and hybridized to a single step-specific probe (Maniatis, T., et al., Cold Spring Harbor Laboratory, Cold Spring Harbor, N.Y. (1982), which is incorporated herein by reference). After detection of the resulting signal, the probe is washed from the membrane and another step-specific probe is hybridized.

Parallel hybridization provides an alternative to this sequential hybridization. The sequencing reactions are divided into a number of aliquots equal to the number of peptide synthesis steps, and run a separate set of lanes for each on the sequencing gel. After transfer of the reaction products to a suitable membrane, the membrane is cut to separate the sets of lanes. Each lane set is then hybridized to one of a plurality of step-specific oligonucleotide probes (see "Uniplex DNA sequencing" and "Multiplex DNA sequencing", in *Plex Luminescent Kits Product Catalog*, Bedford, Mass., 1990, which is incorporated herein by reference).

Amplifying and Sequencing the Oligonucleotide Tags.

On a single synthesis solid support (or an attached bead bearing a tag) there may be only a few hundred copies of each oligonucleotide tag. These may be amplified, e.g., by PCR or other means well known to those skilled in the art, to provide sufficient DNA to be accurately sequenced. The ability to decode the oligomers depends on the number of oligonucleotide identifier tags that can be attached to a bead, the level of amplification that can be achieved from the DNA on a single bead, and the accuracy of sequencing that amplified DNA.

The most commonly used in vitro DNA amplification method is PCR. Alternate amplification methods include, for example, nucleic acid sequence-based amplification (Compton, J. *Nature* 350: 91–92 (1991), which is incorporated herein by reference) and amplified antisense RNA (Van Gelder, R. N. et al., *Proc. Nat. Acad. Sci. USA*, 85:7652–7656 (1988), which is incorporated herein by reference), and the self-sustained sequence replication system (3SR) (Guatelli, J. C., et al., *Proc. Natl. Acad. Sci. USA*, 87: 1874–1878 (1990), which is incorporated herein by reference).

If PCR amplification of an oligonucleotide identifier tag is employed, it is possible to encounter "PCR product contamination", caused by a tiny amount of the product of a PCR reaction finding its way back into a subsequent PCR reaction designed to amplify other tags having the same PCR primer binding sites. One may prevent this problem by introducing lability into the product sequences, and to treat subsequent reactions so as to destroy potential contamination carried over from previous reactions. A specific example of this strategy is to introduce dUMP into the product. Treating each new PCR reaction with uracil-N-glycosidase degrades any dU-containing DNA present, preventing its amplification. The template DNA which contains no dU (only T) is not affected. Of course, the glycosidase is removed before amplification is begun.

The tags described above for peptide synthesis have the unusual characteristic of containing only pyrimidines. This means that the uracil glycosidase strategy (Perkin Elmer Cetus Catalog, Alameda (1991), which is incorporated herein by reference) will work on only half of the strands produced—those containing T's. One cannot introduce dUMP into the complementary, purine-only strand; however, the purine strand is highly vulnerable to acid depurination and alkaline-mediated scission of the backbone. The combination of these treatments can greatly reduce problems with product contamination.

Another approach to preventing carryover contamination is to incorporate a restriction site into the oligo and digest with the corresponding restriction enzyme prior to amplification.

For sequencing amplified DNA it is usually desirable to generate single strand templates. This may be accomplished by several means. One such means is asymmetric PCR, where an excess of one of the primers is used to amplify one strand to a level 10 to 100-fold higher than the other (see, for example, Gyllensten, U. B., and Erlich, H. A., *Proc. Natl. Acad. Sci. USA*, 85: 7652–7656 (1988), and McCabe, P. C., Chapter 10, *PCR Protocols: A Guide to Methods and Applications*. (Innis, M, Gelfand, D., Sninsky, J. and White, T., eds.), Academic Press, San Diego (1990), both incorporated herein by reference). Another means of providing a single strand template is by biotinylating one of the primers and purifying or removing the strand that it primes by adsorption to immobilized streptavidin (*Pierce Immunotechnology Catalog and Handbook*, 1991, which is incorporated herein by reference). Yet another means is to generate RNA transcripts (representing only one of the strands) from an RNA polymerase promoter, and sequence the transcripts with reverse transcriptase (Sommer, S. S. et al., Chapter 25, In *PCR Protocols: A Guide to Methods and Applications*, Academic Press (1990), which is incorporated herein by reference). The particular system described above offers an additional option: the all purine strands can be eliminated by acid/base treatment, leaving the pyrimidine strand for sequencing.

The use of separate sequencing primers for each step-specific oligonucleotide requires a separate, conventional sequencing reaction for each step-specific primer. Using primers that are differentially labeled would allow the identifier tags from a single solid support to be sequenced in a single reaction, and run in a single lane set (2 lanes) on a gel. There are now commercially available primers labeled with distinguishable fluorophores that are suitable for this purpose (ABI Catalog, which is incorporated herein by reference). Sets of chemiluminescent labels now distributed commercially may also be used (Bronstein, I., et al., *BioTechniques*, 8: 310–314 (1990), which is incorporated herein by reference).

DNA sequencing enzymes which may be employed in the present invention include Taq DNA polymerase, *E. coli* DNA polymerase I (Klenow fragment, also referred to as PolK), T7 polymerase, Sequenase™ and Sequenase II™ (Modified T7 DNA polymerases), Bst DNA polymerase, and reverse transcriptase (from AMV, MMLV, RSV, etc., see *USB Enzymes for DNA Sequencing*, U.S. Biochemical Corp, 1991, Cleveland Ohio, incorporated herein by reference).

The sequences may also be identified by a high fidelity DNA hybridization technique. To this end very large scale immobilized polymer synthesis (VLSIPS) with oligonucleotides may be useful.

Screening Receptors with Synthetic Oligomer Libraries

The substrate disclosed herein will have a wide variety of other uses. Merely by way of example, the invention herein can be used in determining peptide and nucleic acid sequences which bind to proteins, finding sequence-specific binding drugs, identifying epitopes recognized by antibodies, and evaluation of a variety of drugs for clinical and diagnostic applications, as well as combinations of the above. Peptides as short as about five amino acids long might be useful in receptor-binding studies, for example.

Synthetic oligomers displayed on small beads can be screened for their ability to bind to receptors. The receptor may be contacted with the library of synthetic oligomers, forming a bound member between the receptor and the oligomer which is able to bind the receptor. The bound member may then be identified. As one example, the receptor may be an immunoglobulin.

The techniques for selection of individual beads displaying ligands on their surface are analogous to methods for cloning mammalian cells expressing cell surface antigens or receptors. Therefore, methods for selecting and sorting beads will be readily apparent to those skilled in the art of cell sorting.

For example, a receptor can be labelled with a fluorescent tag and then incubated with the mixture of beads displaying oligomers. After washing, the beads can be subjected to FACS to identify and physically isolate individual beads showing high fluorescence. Alternatively, affinity adsorption techniques can be employed. The mixture of beads can be exposed to a surface on which receptor has been immobilized. After washing to remove unbound beads, beads bound to the surface can be eluted using conditions which reduce the avidity of the oligomer/receptor interaction (low pH, for example). The process of affinity adsorption can be repeated with the eluted beads if desirable. Finally, individual beads are physically separated, for example, by limited dilution or by FACS. In addition, highly efficient methods for selecting and sorting cells have been described in which cells are incubated with a receptor coupled to small superparamagnetic beads and then cells expressing a ligand for the receptor are extracted using a high power magnet (Miltenyi, S. et al., *Cytometery* 11:231–238 (1990), which is incorporated herein by reference). The magnetically selected cells are then immediately further analyzed and sorted using FACS. Radionucleotides may also serve to label a receptor.

An Automated Instrument for Oligomer Synthesis

The coupling steps for some of the monomer sets (amino acids, for example) require a lengthy incubation time, and a system for performing many monomer additions in parallel is desirable. This can be accomplished with an automated instrument able to perform 50 to 100 parallel reactions (channels). Such an instrument is capable of distributing the slurry of synthesis solid supports, under programmable control, to the various channels for pooling, mixing, and redistribution. Much of the plumbing typical of peptide synthesizers is required, with a large number of reservoirs for the diversity of monomers and the 80 (for 10 step syntheses) oligonucleotide tags typically employed in the present invention. The tag dispensing capability will be capable of translating simple instructions into the proper mixture of oligonucleotides and dispensing that mixture. Monomer building blocks will also be dispensed, as desired, as specified mixtures. Reaction agitation, temperature and time control may be provided.

An appropriately designed instrument may also serve as a multi-channel peptide synthesizer capable of producing 1 to 50 mgs (crude) of up to 100 specific peptides for assay purposes.

EXAMPLE I

SYNTHESIS ON GLASS BEADS OF 4 FLUORESCENTLY TAGGED PENTAPEPTIDES (a) Derivatization of Glass Beads 0.5 g of 3–10 μm diameter silica beads (Polyscience) were washed with refluxing 10% aqueous $HNO_3$ for 20 min. The beads were pelleted and washed with distilled water (5x) and methanol (3x) and dried at 125 degrees C. for 12 hours. Beads were vortexed with 5% solution of aminopropyltriethoxysilane in acetone for 10 hours, pelleted and then washed with acetone (2x), ethanol (5x), methylene chloride (2x) and dried at 125 degrees C. for 45 min. Beads were suspended in dry DMF (1 ml) containing diisopropylethylamine (17 μl, 100 μmoles) and a solution of Fmoc-β-alanine", pentafluorophenyl ester (200 mg, 420 μmoles, Peninsula Labs) in distilled water (1.5 ml) was added. After vortexing for 11 hours beads were pelleted and washed with DMF (3x) and methylene chloride (2x). Beads were treated with a 10% solution of acetic anhydride in DMF containing 0.05 mol % 4-dimethylaminopyridine to cap off any underivatized aminopropyl groups, and then washed with DMF (2x) and methylene chloride (2x). Beads were vortexed with a 20% solution of piperidine in DMF and the release of the Fmoc-piperidine adduct quantitated by monitoring the absorbance spectrum of the supernatant at 302 nm ($\epsilon_{302}$=7800 $M^{-1}$ $cm^{-1}$). An estimate of the degree of substitution of 10 μmoles amino groups/g beads was thus obtained. Finally, the beads were washed with ethanol (5x), methylene chloride (2x) and then dried at 85 degrees C. for 12 hours.

(b) Preparation of Boc-Gly-L-Phe-L-Leu-OH

Glycyl-L-Phenylalanyl-L-leucine (552 mg, 1.5 mmol, Bachem) was dissolved in a solution containing distilled water (10 ml) and 1M NaOH (1.5 ml). The solution was cooled in an ice bath and was treated with a solution of di-tert-butyl pyrocarbonate (337 mg, 1.5 mmol) in p-dioxane (12 ml). A white precipitate rapidly formed but redissolved after stirring at room temperature for 4 hours. The solution was concentrated to dryness in vacuo, the residue taken up in water (5 ml) and the pH adjusted to 2.5 by the addition of 1M $KHSO_4$. The aqueous suspension was extracted with EtOAc (2x, 15 ml), the organic layer separated and dried over $MgSO_4$. After removing the solvent in vacuo the residue was triturated with hexane to afford Boc-Gly-L-Phe-L-Leu-OH as a white solid (yield=642 mg, 98%).

(c) Preparation of Gly-L-Phe-L-Leu Beads

Boc-Gly-L-Phe-L-Leu-OH (44 mg, 0.1 mmol), benzotriazol-1-yloxytris(dimethylamino)phosphonium hexafluorophosphate (44 mg, 0.1 mmol) and 1-hydroxybenzotriazole hydrate (14 mg, 0.104 mmol) were dissolved in dry DMF (1 ml). Diisopropylethylamine (20 µl, 0.115 mmol) was then added and 0.65 ml of this solution immediately transferred to a 0.65 ml microcentrifuge tube containing 80 mg of aminoderivatized glass beads. The sealed tube was vortexed for 3.5 hours, the beads pelleted and washed with DMF (3x) and methylene chloride (2x). The beads were then deprotected with a 50% solution of trifluoroacetic acid in methylene chloride for 30 min, washed with methylene chloride (2x), ethanol (2x), methylene chloride (2x) and dried at 55 degrees C. for 1 hour.

(d) Preparation of Gly-Gly-L-Phe-L-Leu (SEQ ID NO:1) Beads

Fmoc-glycine pentafluorophenyl ester (46 mg, 0.1 mmol) was dissolved in dry DMF (1 ml) containing diisopropylethylamine (17 µl, 0.1 mmol). 0.65 ml of this solution was added to 20 mg Gly-L-PheL-Leu beads in a 0.65 ml microcentrifuge tube and the tube vortexed for 3 hours. The beads were pelleted and washed with DMF (4x) and methylene chloride (2x). Deprotection was effected with a 20% solution of piperidine in DMF for 30 min. The beads were washed with DMF (2x), ethanol (2x), methylene chloride (2x) and dried at 60 degrees C. for 4 hours.

(e) Preparation of L-Pro-Gly-L-Phe-L-Leu (SEQ ID NO:2) Beads

Fmoc-L-proline pentafluorophenyl ester (50 mg, 0.1 mmol) was dissolved in dry DMF (1 ml) containing diisopropylethylamine (17 µl, 0.1 mmol). 0.65 ml of this solution was added to 20 mg Gly-L-PheL-Leu beads in a 0.65 ml microcentrifuge tube and the tube vortexed for 3 hours. The beads were pelleted and washed with DMF (4x) and methylene chloride (2x). Deprotection was effected with a 20% solution of piperidine in DMF for 30 min. The beads were washed with DMF (2x), ethanol (2x), methylene chloride (2x) and dried at 60 degrees C. for 4 hours.

(f) Fluorescein Staining of Gly-Gly-L-Phe-L-Leu (SEQ ID NO:2) Beads 5.4 µg of Gly-Gly-L-Phe-L-Leu beads were suspended in 450 µl of aqueous borate buffer (pH 8.5) and 54 µl of a 10 AM solution of fluorescein isothiocyanate (FITC) added. After vortexing for 1.5 hours, the beads were washed with buffer (5x), ethanol (2x) and methylene chloride (2x). FACS analysis indicated that approximately 10% of available amino groups had been titrated with FITC.

(g) Co-coupling of L-Tyrosine and Biotin to Mixture of L-Pro-Gly-L-Phe-L-Leu (SEQ ID NO:2) and FITC labelled Gly-Gly-L-Phe-L-Leu (SEQ ID NO:1) Beads 5 mg of FITC labelled Gly-Gly-L-Phe-L-Leu (SEQ ID NO:1) beads and 5 mg L-Pro-Gly-L-Phe-L-Leu (SEQ ID NO:2) beads were mixed together in a single tube, vortexed with a 0.1 mM solution of diisopropylethylamine in methylene chloride and the suspension was divided into two equal portions. The beads were pelleted and to one portion was added a solution containing Fmoc-O-tert-butyl-L-tyrosine pentafluorophenyl ester (59 mg, 95 µmol), N-hydroxysuccinimidobiotin (1.7 mg, 5 µmol) and diisopropylethylamine (17 µl, 100 µmol) in dry DMF (1 ml). After vortexing for 3 hours the beads were washed with distilled water (2x), ethanol (2x), methylene chloride (2x) and DMF (1x). Fmoc deprotection was effected with a 20% solution of piperidine in DMF for 30 min and tert-butyl side chain protecting groups were removed by treatment with 25% trifluoroacetic acid in methylene chloride for 30 min. The pelleted beads were washed with methylene chloride (2x), ethanol (2x), and TBS (1x).

(h) R-Phycoerythrin Staining of Biotinylated L-Tyr-(Gly/L-Pro)Gly-L-Phe-L-Leu Beads (SEQ ID NO:3)

Biotinylated L-tyrosine beads from (g) above were suspended in TBS (0.5 ml) and treated with 10 µl of R-phycoerythrin-avidin conjugate (Molecular Probes) for 30 min. Pelleted beads were washed with TBS (5x).

(i) Co-coupling of L-Proline and Biotin to Mixture of L-Pro-Gly-L-Phe-L-Leu (SEQ ID NO:2) and FITC labelled Gly-Gly-L-Phe-L-Leu (SEQ ID NO:1) Beads 5 mg of a mixture of L-Pro-Gly-L-Phe-L-Leu (SEQ ID NO:2) and FITC labelled Gly-Gly-L-Phe-L-Leu (SEQ ID NO:1) beads were treated with a solution containing Fmoc-L-proline pentafluorophenyl ester (48 mg, 95 µmol), N-hydroxysuccinimidobiotin (1.7 mg, 5 µmol) and diisopropylethylamine (17 µl, 100 µmol) in dry DMF (1 ml). After vortexing for 3 hours the beads were washed with DMF (2x), ethanol (2x), methylene chloride (2x) and DMF (1x). Fmoc deprotection was effected with a 20% solution of piperidine in DMF for 30 min and by way of control the beads were treated with 25% trifluoroacetic acid in methylene chloride for 30 min. The pelleted beads were washed with methylene chloride (2x), ethanol (2x) and TBS (1x).

(j) Tri-Color Staining of Biotinylated L-Pro-(Gly-L-Pro)-Gly-L-Phe-L-Leu Beads

Biotinylated L-proline beads from (i) above are suspended in TBS (0.5 ml) and treated with 20 µl Tri-Color: streptavidin conjugate (Caltag Labs) for 30 min. Pelleted-beads are washed with TBS (5x).

(k) Selection of Beads containing Peptide Ligands for Monoclonal Antibody 3E7

Monoclonal antibody 3E7 was raised against the opioid peptide b-endorphin. Its binding specificity has been well characterized by solution assays with chemically synthesized peptides. Table 1 lists the equilibrium binding constants (Kd) of the peptides considered here. Only the peptide YGGFL shows appreciable affinity for the antibody.

TABLE 1

| Peptide | YGGFL (SEQ ID NO:5) | YPGFL (SEQ ID NO:6) | PPGFL (SEQ ID NO:7) | PGGFL (SEQ ID NO:8) |
| --- | --- | --- | --- | --- |
| Kd | 6.6 nM | >1 mM | >1 mM | >1 mM |

A mixture of beads containing either YGGFL, YPGFL, PGGFL, or PPGFL and their respective tags (see above) are added in phosphate buffered saline (PBS) containing monoclonal antibody 3E7 that has been previously conjugated to colloidal superparamagnetic microbeads (Miltenyi Biotec, West Germany). After a 16 hr incubation at 4 degrees C., beads which bind the 3E7 antibody are selected using a high strength magnet. The selected beads are then analyzed by flow cytometry. Analysis of the selected beads reveals that they contain both fluorescein and R-phycoerythrin, indicating that only beads displaying the peptide YGGFL are selected by the 3E7 antibody.

EXAMPLE 2

SYNTHESIS ON GLASS BEADS OF 4 PENTAPEPTIDES TAGGED WITH OLIGONUCLEOTIDE IDENTIFIERS (a) Synthesis of Identifier Oligonucleotides (I)–(IV)

(I) 5'-B$^1$B$^2$-CTTTCT<u>TCCTCTCCCTCTTTTCTCCTCT</u>CTTTTTTCTC CTTTCTTTTTTCTCTCCCTCTCTC-CTCTCTCccctttctctcctttc ct <u>CCTCTCCTCTCTCTCTTCTTTCC</u>-3'(SEQ ID NO:9)

(II) 5'-B$^1$B$^2$-CTTTCT<u>TCCTCTCCCTCTTTTCTCCTCT</u>TCTTTTTTCTC CTTTCTTTTTTCTCTCCCTCTCTC-CTCTCTCccctttctctcctttc ct <u>CCTCTCCTCTCTCTCTTCTTTCC</u>-3'(SEQ ID NO:10)

(III) 5'-B$^1$B$^2$-CTTTCT<u>TCCTCTCCCTCTTTTCTCCTCT</u>TTCTTTTTCTC CTTTTCTTTTTCTCTCCCTCTCTC-CTCTCTCtcttcctttccccctct ct <u>CCTCCTCTCCTCTCTCTTCTTTCC</u>-3'(SEQ ID NO:11)

(IV) 5'-B$^1$B$^2$-CTTTCT<u>TCCTCTCCCTCTTTTCTCCTCT</u>CTTCTTTTTCTCC CTTTCTTTTTTCTCTCCCTCTCTC-CTCTCTCtcttcctttccccctct ctctct <u>CCTCTCCTCTCTCTCTTCTTTCC</u>-3'(SEQ ID NO:12)

Where: B$^1$=p-Maleimido-C$_6$H$_4$—(CH$_2$)$_3$—C(O)NH—(CH$_2$)$_6$—O—PO$_2$—O—
B$^2$=CH$_2$—CH[(CH$_2$)$_4$—NH-Biotin]-CH$_2$—O—PO$_2$—O—

The regions complementary to the 5' and 3' PCR primers are underlined. The regions complementary to the step-specific sequencing primers are shown in lower case: there are two steps specified in this example. The monomer encoding region is shown in bold type: CT7 encodes Gly, TCT$_6$ encodes L-Pro, and TTCT$_5$ encodes L-Tyr in this case. Thus oligos (I)–(IV) code respectively for Gly in position 2, L-Pro in position 2, L-Tyr in position 1 and L-Pro in position 1.

Oligos (I)–(IV) are synthesized on an ABI PCR-mate synthesizer using commercially available (Sigma) DMT-O-Me phosphoramidites. The N$^4$-amino group of cytidine is protected as the benzoyl derivative. The 5' terminal (B1) and penultimate (B2) phosphoramidites are respectively N-MMT-C$_6$-AminoModifer (Clonetech) and Biotin Phosphoramidite (Glen Research) for each oligonucleotide. The fully protected O-methyl phosphotriester oligomers are cleaved from the CPG support by treatment with concentrated NH$_4$OH at 25 degrees C. for 1 hour. The crude products are purified by affinity chromatography on a monomeric avidin-agarose column (Pierce) and the full-length material is eluted with 2 mM biotin. The 5'-MMT group is removed by treatment with 80% acetic acid for 1 hour at 25 degrees C. and the solution is evaporated to dryness. The products are dissolved in PBS, pH 8.0, and treated with a 50-fold excess of succinimidyl 4-(p-maleimidophenyl) butyrate (Pierce) in DMF for 30 min. The modified, protected oligonucleotides are desalted by RP-HPLC, lyophilized and stored under nitrogen.

The primers used for PCR and sequencing are prepared in the normal fashion and are shown below:

5' PCR Primer 5'-TCCTCTCCCTCTTTTCTCCTCCT-3' (SEQ ID NO:13)

3' PCR Primer 5'-Biotin-GGAAAGAAGAGGGAAA GGAGAGG-3'(SEQ ID NO:14)

Step #1 Sequencing Primer 5'-AGAGAGGGGAAA GGAAGA-3'(SEQ ID NO:15)

Step #2 Sequencing Primer 5'-AGGAAAGGAGAGAAA GGG-3'(SEQ ID NO:16)

(b) Preparation of Gly-Gly-L-Phe-L-Leu (SEQ ID NO:1) Beads Bearing Identifier Oligo (I)

5 mg of Gly-L-Phe-L-Leu beads are treated with a solution containing Fmoc-Gly-OH (99.95 μmol), Fmoc-Cys (Npys)-OH (0.05 μmol, Calbiochem), benzotriazol-1-yloxytris-(dimethylamino)phosphonium hexafluorophosphate (100 μmol), 1-hydroxybenzotriazole hydrate (100 μmol) and diisopropylethylamine (150 μmol) in dry DMF (1 ml) for 2 hours. The beads are washed with DMF (2x), methanol (2x) and then treated with a 10 mM DTT solution in methanol for 30 min to deprotect the cysteine residues. The beads are quickly washed with ice-cold methanol (2x), pelleted and then reacted for 20 min with 100 μl of a 0.1 mM solution of oligo (I) in methanol. After washing with methanol (2x) and DMF (2x) the beads are deprotected for 20 min with 20% piperidine in DMF. Finally, the beads are washed with DMF (2x), methanol (2x), methylene chloride (2x) and dried at 45 degrees C. for 1 hour.

(c) Preparation of L-Pro-Gly-L-Phe-L-Leu (SEQ ID NO:2) Beads Bearing-Identifier Oligo (II)

5 mg of Gly-L-Phe-L-Leu beads are treated as in (b) above, substituting Fmoc-L-Pro-OH and Oligo (II) for Fmoc-Gly-OH and Oligo (I) respectively.

(d) Preparation of (O$^t$Bu)-L-Tyr-(Gly/L-Pro)-Gly-L-Phe-L-Leu (SEQ ID NO:4) Beads Bearing Identifier Oligos (III and I/II)

Beads from (b) and (c) are pooled and divided into two equal portions. One portion is treated as in (b), substituting Fmoc(OtBu)-L-Tyr-OH and Oligo (III) as appropriate.

(e) Preparation of L-Pro-(Gly/L-Pro)-Gly-L-Phe-L-Leu Beads (SEQ ID NO:4) Bearing Identifier oligos (IV and I/II)

The second pool is treated as before, substituting Fmoc-L-Pro-OH and Oligo (IV) as appropriate.

(f) Reconstitution and Deprotection of the Peptide Library

Beads from (d) and (e) are pooled and the phosphate, amino acid side-chain and nucleotide exocyclic amino protecting groups are removed as follows. A one hour reaction with a 1:2:2 mixture of thiophenol: triethylamine: p-dioxane is followed by washing with methanol (2x), methylene chloride (2x) and then treated for 5 min with 95:5 trifluoroacetic acid: ethanedithiol. After washing with methanol (3x), the beads are treated at 55 degrees C. with 1:1 ethylenediamine: ethanol for 1 hour, and washed with ethanol (2x) and PBS (2x). This collection of beads constitutes the library and contains approximately equal quantities of the 4 immobilized peptides YGGFL, YPGFL, PGGFL and PPGFL. Additionally each bead carries two distinct 113 bp oligonucleotide sequences encoding the identities of both the first and second amino acids on that bead.

PCR Amplification of Oligonucleotide Identifier Tag

After FAC sorting of affinity purified beads into individual 0.5 ml polypropylene tubes, 25 μl of TBS containing 0.1 μg salmon sperm DNA (as carrier) is added together with 25 μl of 2xPCR Amplification Buffer. The 2xbuffer contains:

100 mM KCl
20 mM Tris-Cl, pH 8.4, 20 degrees C.
6 mM MgCl$_2$
0.4 mM dNTP's
1 μM 5' PCR primer
1 μM 3' PCR primer
100 units/ml Taq DNA polymerase After buffer addition, the sample is covered with 50 μl of mineral oil and transferred to an automated thermal cycler. In the thermal cycler the samples are heat denatured at 95 degrees C. for 2 min, and then cycled 35 times through 3 steps: 95 degrees C./30 sec, 60 degrees C./1 min, 72 degrees C./1 min, followed by 72 degrees C. for an additional 5 min and then cooled and held at 15 degrees C. until ready for processing on streptavidin beads. The mixture is heated to 95 degrees C. to denature the strands and the biotinylated purine strand plus excess 3' PCR primer is removed by addition of streptavidin-coated beads, and the tubes are spun at 12K rpm for 5 min. The supernatant is used in the sequencing reactions as described below.

Sequencing of PCR Amplified Oligonucleotide Tags

The amplified oligonucleotides from individual bead isolates are sequenced in a pair of reactions (using ddA or ddG as chain terminators) with either the Step #1-specific or the Step #2-specific sequencing primers.

(i) Annealing Template and Primer

For each set of two sequencing lanes, a single annealing and subsequent labeling reaction is run by combining 8.5 μl sequencing primer (conc=0.25 pmol/μl), 1.5 μl Sequenase 5× sequencing buffer (200 mM Tris HCl pH 7.5, 100 mM MgCl$_2$, 250 mM NaCl) and 10 μl template DNA from the amplification supernatant above. The samples are heated for 2 minutes at 65 degrees C. and allowed to cool slowly to room temperature (approx 10 minutes).

(ii) Labeling Reaction

20 Sequenase (v2.0) is diluted 1:20 with TE (10 mM Tris HCl pH 7.5, 1 mM EDTA) and a labeling cocktail containing a 2:3.5 ratio of diluted enzyme to labeling mix (i.e. 4:2:1 mixture of 150 nM dGTP, 0.1 M dithiothreitol, alpha-$^{35}$S-dATP, >1000 Ci/mmol) is prepared. 5.5 μl of the cocktail is incubated with 10 μl annealed template/primer (from (i)) at 25 degrees C. for 5 min.

(iii) Termination Reactions

6 μl of labeling reaction mixture is added to 5 μl of each of the appropriate ddXTP termination reaction mixes (i.e. 80 μM dGTP, 80 μM dATP, 50 mM NaCl and 8 μM ddGTP or 8 μM ddATP). After incubation at 37 degrees C. for 5 min, 8 μl of Stop Solution (95% formamide, 20 mM EDTA, 0.05% bromophenol blue, 0.05% xylene cyanol) is added to each of the termination reactions.

(iv) Gel Solutions

The sequencing gel is comprised of 6% total acrylamide [19:1 Acrylamide/Bis], 0.09 M Tris base, 0.09 M boric acid, 1 mM EDTA and 7 M urea. The gel is polymerized by addition of 1.9 μl of 25% ammonium persulfate per ml and 0.72 μl of TEMED per ml of above gel solution. The gel is allowed to polymerize at least one hour and is prerun at least 20 minutes prior to sample loading. Gel plates are then maintained between 40 and 50 degrees C. prior to and during the run.

(v) Sample Prep

Reactions are heated to 85–95 degrees C. for 2 minutes prior to loading, and the gel is run until the bromophenol blue dye reaches the bottom of the gel. The sequences of interest lay between the bromophenol and xylene cyanol markers. The information required to identify the sequence of monomers in the oligomers attached to the bead is contained in the DNA sequence information.

Although the present invention has been described in some detail by way of illustration and example for purposes of clarity and understanding, it will be apparent that certain changes and modifications may be practiced within the scope of the appended claims.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method of preparing a library of diverse compounds, each of said compounds being prepared by step-by-step assembly of building blocks, said method comprising the steps of:
- a) apportioning solid supports among a plurality of reaction vessels; and
- b) in each reaction vessel of said plurality of reaction vessels, exposing said supports to a plurality of first building blocks and to a plurality of first identifier tags under conditions compatible with immobilization of the first building block and the first identifier tag,
    wherein said first building block is capable of being covalently coupled to a second building block or a second identifier tag;
    wherein said first identifier tag does not interfere with the coupling of said first building block to said second building block or said second identifier tag;
    wherein said first identifier tag in each of said reaction vessels identifies the first building block present in that vessel; and,
    wherein the first building block present in one reaction vessel is chemically different from the first building block found in the other reaction vessels.

2. The method of claim 1, wherein said first building block is an amino acid.

3. The method of claim 2, wherein said amino acid is selected from the group consisting of L-amino acids, D-amino acids, alpha-amino acids, beta-amino acids, and omega amino acids.

4. The method of claim 1, wherein said first identifier tag has a recognizable feature due to a physical property of said tag, said physical property selected from the group consisting of size, shape, color, optical density, differently absorbing or emitting of light, and chemical reactivity.

5. The method of claim 4, wherein said first identifier tag comprises a fluorophore.

6. The method of claim 5, wherein said first identifier tag is a nucleotide or an oligonucleotide.

7. The method of claim 6, wherein said first identifier tag is an oligonucleotide from 3 to 10 nucleotides in length.

8. The method of claim 6, wherein said first identifier tag is an oligonucleotide from 50 to 150 nucleotides in length.

9. The method of claim 1, wherein said first identifier tag is added before, or after the addition of said first building block.

10. The method of claim 1, wherein said first identifier tag is coupled to another identifier tag.

11. The method of claim 1, wherein said first identifier tag is coupled to said solid support and not to another identifier tag.

12. The method of claim 1, wherein said solid support is a bead or particle.

13. The method of claim 12, wherein said solid support is a nonporous bead.

14. The method of claim 13, wherein said solid support is a bead with a diameter in the range of 1 nm to 1 mm.

15. The method of claim 1, wherein prior to exposing said first building block to said supports, said first building block is activated to facilitate immobilization of the building block onto said support.

16. The method of claim 1, wherein prior to exposing said first identifier tag to said supports, said first identifier tag is activated to facilitate immobilization of the identifier tag onto said support.

17. The method of claim 16, wherein said first identifier tag is a nucleotide or an oligonucleotide and said first identifier tag is activated to form a phosphoramidite group prior to exposure of the tag to the support.

* * * * *